United States Patent [19]

Jones et al.

[11] Patent Number: 5,412,088
[45] Date of Patent: May 2, 1995

US005412088A

[54] 6-O-SUBSTITUTED GUANOSINE DERIVATIVES

[75] Inventors: Roger A. Jones, Glenside, Pa.; Reza Fathip, Newark; Barbara L. Gaffney, Neshanic, both of N.J.

[73] Assignee: Rutgers, The State University, New Brunswick, N.J.

[21] Appl. No.: 863,653

[22] Filed: Apr. 3, 1992

Related U.S. Application Data

[63] Continuation of Ser. No. 439,616, Nov. 20, 1989, abandoned.

[51] Int. Cl.$^6$ ............... C07H 19/167; C07H 19/173; C07H 19/20; C07H 21/04
[52] U.S. Cl. ................... 536/27.81; 536/24.3; 536/25.3
[58] Field of Search ............ 536/23, 24, 26, 27–29, 536/28.1, 24.3, 25.3

[56] References Cited

U.S. PATENT DOCUMENTS 4,962,194 10/1990 Bridges .................... 536/27.11

OTHER PUBLICATIONS

Hanna et al., "J. Heterocyclic Chem.", 25, 1899 (1988).
Chollet, "Nucleic Acids Research", vol. 16, No. 1, 1988.
Chollet et al, "Synthetic Oligonucleotides in Molecular Biology", Uppsala, Sweden, 18–24 Aug. 1985.
Gaffney et al., "Tetrahedron", vol. 40, No. 1, p. 3, 1984 at p. 7.
Gaffney and Jones, "Biochemistry", 1989, 28, 5881 at 5883.
Reese et al., "J. Chem. Soc. Perkin Trans I", 1984, 1263.
Bridson et al., "J.C.S. Chem. Comm.," 1977, 791.
Gaffney and Jones "Tetrahedron Letters", vol. 29, No. 22, pp. 2619–2622, 1988.
Adamiak, et al., "Synthetic Oligonucleotides in Molecular Biology", Uppsala, Sweden 18–24 Aug. 1985.
Vorlickova et al., "Nucleic Acids Res.", 16, (1988), 279.
Cheong et al., "Nucleic Acids Res.", 23, (19880 5115).
Howard et al., "Biochemistry", 23, (1984) 6723.
Daskalov et al., "Tetrahedron Lett.", 21, (1980) 3899.

*Primary Examiner*—Douglas W. Robinson
*Assistant Examiner*—Gary L. Kunz
*Attorney, Agent, or Firm*—Lerner, David, Littenberg, Krumholz & Mentlik

[57] ABSTRACT

The following species of N6-activated guanosine derivatives are disclosed:

2-N-trifluoroacetamido-6-(4-nitrophenoxy)-9-(2-deoxy-beta-D-erythro-pentofuranosyl)purine 2-N-trifluoroacetamido-6-pentafluorophenoxy-9-(2-deoxy-beta-D-erythro-pentofuranosyl)purine 6-dimethylpyridinium-9-(2-deoxy-beta-D-erythropentofuranosyl)purine These guanosine compounds are useful as precursors in the synthesis of a wide variety of antiviral and anticancer nucleosides such as 2-amino-2-deoxyadenosine or 6-thio-deoxyguanosine. Also disclosed are oligonucleotides containing the above nucleosides which are precursors to modified oligonucleotides which are useful as hybridization probes.

32 Claims, No Drawings

6-O-SUBSTITUTED GUANOSINE DERIVATIVES

This is a continuation of application Ser. No. 07/439,616, filed Nov. 20, 1989, now abandoned.

BACKGROUND AND SUMMARY OF THE INVENTION

FIELD OF THE INVENTION

The invention relates to the field of substituted guanosine derivatives and methods for their production.

BACKGROUND OF THE INVENTION

One of the recurring problems in biochemistry is the availability of raw materials. Not surprisingly, of particular interest are raw materials corresponding to the basic building blocks fundamental to biochemistry, such as nucleosides and nucleotides of the naturally occurring purines and pyrimidines found in deoxyribonucleic acids (DNA) and ribonucleic acids (RNA). For the purposes of this application, a monomeric unit consisting of a nitrogenous heterocyclic base which is derived from either a purine or a pyrimidine, a pentose, and a molecule of phosphoric acid is known as a nucleotide. A nucleoside is the same as a nucleotide except for the absence of the phosphoric group. Experimentation on nucleosides or nucleotides may take the form of structural and functional analysis of derivatives such as the identification of potential antitumor activity associated with several 6-thioguanine nucleosides. See Hanna, et al, "A Convenient Synthesis of 2'-Deoxy-6-thioguanosine, Ara-Guanine, Ara-6-Thioguanine and Certain Related Purine Nucleosides by the Stereospecific Sodium Salt Glycosylation Procedure," *J. Heterocyclic chem.*, 25, 1899 (1988).

Alternatively, nucleotides having specific properties may be inserted or attached to various probes or small sections of polynucleotides such that their effects may be monitored or their corresponding base pairs located For example, Chollet, "DNA Containing the Base Analog 2-Aminoadenine: Preparation, Uses, Hybridization Probes and Cleavage By Restriction Endonucleases," *Nucleic Acids Research*, Vol. 16, No. 1, 1988, p. 305, discusses that modified bases can be incorporated into DNA by chemical or enzymatic procedures. These modified 2'-deoxy-guanosine derivatives are shown to be good substrates for in vitro DNA polymerase I mediated enzymatic syntheses and allow for preparation of DNA containing 2-aminoadenine at defined sites on DNA strands. These probes having defined sequences are important tools for the identification and isolation of specific DNA sequences. The introduction of a stabilizing DNA duplex produced with the 2-amino-adenosine also allows for the use of more stringent hybridization conditions, and therefore increases the probes specificity for its target.

Of particular interest to researchers are modifications of the active bonding sites in purines and pyrimidines, such as, for example, those in the 6th and 2nd position in a purine. Unfortunately, the production of stable nucleosides has been historically plagued with a long list of problems. This is particularly true of 6-substituted guanosine nucleosides. These problems include cost, efficiency and specificity.

For example, Chollet et al discussed a route for synthesis of 2-amino-2-deoxyadenosine derivatives via 2-amino-6(N-pyridinium)purine-2'-deoxyribosides in a paper entitled "Synthesis of Oligodeoxyribonucleotides Containing the Base 2-Aminoadenine," presented at the second International Conference on "Synthetic Oligonucleotides in Molecular Biology," Uppsala, Sweden, 18–24 Aug. 1985, at page two thereof. As discussed therein, the formation of the 6-amino-substituted purine required treatment with ammonia in water and dioxane for three days, and resulted in the production of only trace amounts of 2-amino-2'-deoxyadenosine. The remainder of the product was a base protected form having an isobutyryl group on the nitrogen bonded in the 2nd position to the purine. This is the "$N^2$" nitrogen. The isobutyryl group is extremely difficult to cleave from the $N^2$ due to its slow hydrolysis. In fact, complete cleavage of the $N^2$ isobutyryl group may require over 7 days of heating in concentrated aqueous ammonia. Id. at page 2, ($NH_3$ in $H_2O$ (min. conc. 25–30%) at 65° C. for 7 days). See also Gaffney et al., "The Influence of the Purine 2-Amino Group on DNA Conformation and Stability—II", *Tetrahedron*, Vol. 40, No. 1, p 3, 1984 at p 7. Obviously, such inefficient synthesis routes produce costly end products. Furthermore, the presence of the isobutyryl group is a limiting factor in the usefulness of protected amino purines because the isobutyryl group will prevent hydrogen bonding between base pairs. See also Gaffney and Jones "Thermo-dynamic Comparison of the Base Pairs Formed by the Carcinogenic Lesion $O^6$-Methylguanine with Reference Both to Watson-Crick Pairs and to Mismatched Pairs," Biochemistry, 1989, 28, 5881 at 5883. (Incomplete deprotection occurs because the isobutyryl group $N^2$ protecting group is cleaved "exceptionally slowly, particularly in an oligonucleotide." Id.)

One remedy for the situation was reported directly above in Gaffney and Jones by the use of an $N^2$-acetyl-$O^6$-methyl-2'-deoxyguanosine. The $N^2$-acetyldeoxyguanosine was synthesized by suspending deoxyguanosine in pyridine (40 mL per mmol deoxyguanosine) and 4-dimethylaminopyridine (0.1 mmol per mmol deoxyguanosine), triethylamine (11 mmol per mmol deoxyguanosine) and acetic anhydride (10 mmol per mmol deoxyguanosine) are added and the mixture is heated at 50° for 20 hours. This gives 2-N,3'-O,5'-triacetyl-2'-deoxyguanosine in 76% yield. However, while the $N^2$-acetyl group is easier to remove than the isobutyryl group, it is still slow and problematic.

Furthermore, individual routes or mechanisms are required for each individual desired end product. That is to say that specific methodologies must be developed for each corresponding element to be added in the 6th position of a quanine nucleoside. For example, Hanna et al., supra describes a pathway for the conversion of a chlorinated purine to a 6-thioquanosine and to a guanine nucleoside or nucleotide. The process utilizes commercially available 6-chloropurine or 2-amino-6-chloropurine which were glycosylated to form the corresponding nucleoside intermediates. These are then converted into 2'-deoxy-6-thiopurine nucleosides by direct nucleophilic displacement. In addition to being very specific and therefore limited in applicability, the synthesis of Hanna et al is quite time consuming. (over 18 hours to obtain the 6-chlorinated nucleoside (61% yield) and an additional approximately 3 hours thereafter.)

Another route was suggested in Reese et al. "The Protection of Thymine and Guanine Residues in oligo-deoxyribonucleotide Synthysis," *J. Chem. Soc. Perkin Trons.* I, 1984, 1263 wherein 2-Deoxyguansine is converted in five steps into its 6-O-(2-nitrophenyl)-2-N- phenylacetyl and crystalline 6-O-(3,5-dichlorophenyl)-2-N-phenylacetyl derivatives, respectively, in 39 and 42% overall yields, respectively. The 6-O-(2-nitrophenyl derivative was produced by a multistep process in which triethylamine was added to a stirred suspension of 3',5'-di-O-methoxyacetyl-2'-deoxyguanosine and mesitylene-2-sulphonylchloride in dry acetonitrile. After reaction, cooling, extraction, drying and fractioning under pressure, the resulting sulfonated derivative was dissolved in pyridine and diisopropylethylamine and 2-nitrophenol. This mixture was then heated under reflux for 1 hour, cooled, and separated. After several more steps including a series of washing and elutions; and a reaction with 2,6-Lutidine and phenylacetylchloride in acetonitrile, the aforementioned compound was produced.

A modified procedure was used to produce the 6-O-(3,5-dichlorophenyl) derivative. This process, however, also involved the use of Mesitylene-2-sulphonylchloride to produce a first, sulfur continuing guanine nucleoside derivative. See Id. at 1268.

Also of interest with regard to substituted guanine nucleosides is a paper by Bridson et al., "Acylation of 2',3',5'-Tri-O-acetylguanosine," *J.C.S. Chem. Comm.*, 1977, 791 which cites the Reese et al. paper discussed above. Accordingly, an unreacted guanosine was reacted with an unsubstituted acetic anhydride in a solvent of pyridine to give 2',3',5'-tri-O-acetylguanosine. This compound can undergo further acylation in the $N^2$ position to yield the tetra acetyl derivative. Acylation of the 6th position, however required the treatment of triacetyl derivative with an excess of 2,6-dichlorobenzoyl chloride in a pyridine solution which yields the O(6)-aroyl derivative. This derivative appears, however, to be unprotected in the $N^2$ position. In another procedure, the tri-acetyl derivative is reacted with methanesulphonyl chloride in a pyridine solution to yield the O(6)-mesyl derivative. The paper left open the question of why the tri-substituted guanine nucleoside is attacked by some acylating agents in the $N^2$ position and others in the O(6) position. They appear to have been unable to produce compounds substituted in both positions. The paper suggests the possibility of O(6)-acylguanosine derivatives being useful as intermediates and discusses the succeptability of the mesitylenesulphonyl derivative to nucleophitic substitution to yield a compound substituted in the 6th position with inter alia a secondary amine. However, the methods described are insufficient to actually convert the acylated products to other useful products and intermediates such as those of the present invention.

Another long standing problem in DNA/RNA research is the lack of a convenient methodology for adding substituted and $N^2$ protected quanine nucleosides into an oligonucleotide and subsequently removing at least the $N^2$ protecting group therefrom. This protecting group may serve as a block which prevents the formation of hydrogen bonds between corresponding base pairs on a plurality of oligonucleotides. Often the methodologies currently available are time consuming and may adversely effect the oligonucleoside. There has also been a lack of compositions which could make such a method practicable.

Another problem which is closely related is that of "marking" or "labeling". Marking or labeling is useful for identification of reaction pathways by permitting an easy way of determining the status of a marked or labeled compound. Labeled compounds may also be useful in a quantification of labeled reaction products. Unfortunately, synthesis of labeled compounds is often difficult, time consuming and expensive. When combined with the problems and technologies associated with the formation of substituted guanine nucleosides, it can be readily appreciated that the subject matter may become unworkable.

In addition, there remains a need for a quick, high-yield procedure which will allow for the production of a wide variety of 6-substituted guanine nucleosides and nucleotides from a single convenient protocol. Furthermore, there remains a need for the creation of shelf- and storage-stable guanosine reaction intermediates capable of being further processed to form desirable end products such as 2-amino-2'-deoxyadenosine or 2-aminoadenosine, or which may alternatively be used for the formation of other nucleoside derivatives. Therefore, there remains a need to produce labeling compounds which may be easily produced and easily incorporated into oligonucleosides.

SUMMARY OF THE PREFERRED EMBODIMENTS

Therefore, it is one object of the present invention to provide for compositions of matter and processes which may be useful for the formation of 2,6-diamino-9-[saccharide]purines or other 6-substituted $N^2$ amino guanine nucleosides.

It is another object of the present invention to provide compositions which may be directly inserted into DNA or RNA and thereafter, conveniently converted to useful forms.

It is another object of the present invention to provide compositions which are useful as fluorescent markers or labels.

It is another object of the present invention to provide a process of producing 2,6-diamino-9-[saccharide]-purine.

It is also an object of the present invention to provide a process of producing a guanine nucleoside substituted in the 6th position.

Another object of the present invention is a process of producing 6-(nitrophenoxy)-9-[saccharide]purine having a nitro group in the 3, 4 or 5 position.

It is another object of the present invention to provide a process of producing 6-(substituted halophenoxy-9-[saccharide]purine.

In accordance with these objects, as well as others which will be readily apparent to the skilled artisan, the present invention provides a composition of matter having the structure of the formula (I):

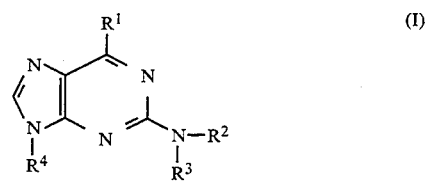

wherein $R^1$ is a substituted or unsubstituted nitrophenoxy group having a nitro group in the 3, 4 or 5 position, or a pentafluorophenoxy group. $R^2$ is an electron withdrawing group, H, a substituted or unsubstituted aliphatic compound having from about 1 to about 20 carbons or a substituted or unsubstituted aromatic compound having from about 1 to about 20 carbons; $R^3$ may be the same as or different from $R^2$ and may be an electron withdrawing group, H, a substituted or unsubstituted aliphatic compound having from about 1 to about 20 carbons, or a substituted or unsubstituted aromatic compound having from about 1 to 20 carbons; and $R^4$ is a substituted or unsubstituted saccharide.

In accordance with another aspect of the present invention, there is provided a composition of matter having a structure of the formula (I):

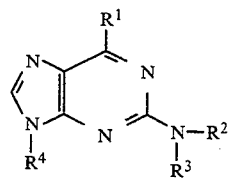

wherein $R^1$ is a nucleophile capable of binding at the 6th position of a purine ring system without cleaving $R^2$; $R^2$ is an electron withdrawing group whose corresponding carboxylic acid has a $pK_a$ less than that of acetic acid, $R^3$ may be the same as or different from $R^2$ and may be an electron withdrawing group, H, a substituted or unsubstituted aliphatic compound having from about 1 to about 20 carbons, or a substituted or unsubstituted aromatic compound having from about 1 to 20 carbons; and $R^4$ is a substituted or unsubstituted saccharide.

Further in accordance with another aspect of the present invention, there is provided a composition of matter as described immediately above, wherein $R^1$ is a substituted or unsubstituted nitrophenoxy group having a nitro group in the 3, 4 or 5 position, a non-sterically hindered compound having a structure of the formula (II):

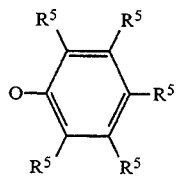

wherein $R^5$ comprises a halogen or hydrogen and wherein at least three $R^5$ groups are halogens, an aromatic tertiary amine, or an aliphatic tertiary amine.

Also in accordance with the present invention, there is provided a composition of matter having a structure of formula (I):

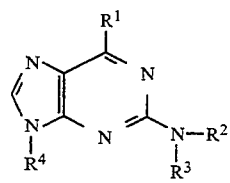

wherein $R^2$ and $R^3$ may be the same or different and comprise H, a substituted or unsubstituted aliphatic compound having from about 1 to about 20 carbons, or a substituted or unsubstituted aromatic compound having from about 1 to 20 carbons; $R^4$ is a substituted or unsubstituted saccharide; and wherein $R^1$ is selected from the group consisting of $(CH_3)_2NC_5NH_4-$, a substituted or unsubstituted nitrophenoxy group having a nitro group in the 3, 4 or 5 position, or a pentafluorophenoxy group.

In a particularly preferred aspect of the present invention, compositions are provided wherein $R^1$ is a 4-nitrophenoxy group and $R^2$ is a trifluoroacetyl group. In another preferred aspect thereof, $R^1$ is a pentafluorophenoxy group and $R^2$ is a trifluoroacetyl group.

In accordance with another aspect of the present invention there is provided a composition of matter 2-N-trifluoracetamido-6-(4-nitrophenoxy)-9-(2-deoxy-beta-D-erythro-pentofuransoyl)pyrine and a composition or matter 2-N-(trifluoroacetamido-6-pentafluorophenoxy)-9-(2-deoxy-beta-D-erythro-pentofuranosyl)-purine.

In accordance with another aspect of the present invention there is provided a composition of matter 2-N-trifluoracetamido-6-(4-nitrophenoxy)-9-(ribo)purine and a composition of matter 2-N-trifluoracetamido-6-(pentafluorophenoxy)-9-(ribo)purine.

These compositions have uses and advantages far in excess of expectations. Specifically, these compounds may be produced quickly, (i.e. the pyridyl compound may be formed in less than about two hours and the pentafluorophenoxy derivatives were formed in between about 24-48 hours) in high yield (i.e. in excess of 67%) from conventional and commercially available starting materials with little or no effort. Many of the compounds produced according to the present invention are shelf/storage stable and may be prepared in advance for subsequent use.

These uses may include, without limitation, the formation of other 6 substituted guanine nucleosides such as, for example, 2,6-diamino-9-(2-deoxy-beta-D-erythro-pentofuranosyl)purine which is useful in stability studies of DNA, as well as the ribose derivative which is similarly useful for RNA. Other uses include those previously discussed. Furthermore, from these compounds various fluorescently labeled compositions and compositions having potential anti-tumor activity may be produced.

Furthermore, some of these compositions may be quickly, conveniently and easily inserted into or attached to an oligonucleotide and, thereafter, converted to another form, (deprotected), in situ.

Other compounds, in accordance with the present invention, are particularly useful as intermediates for the formation of such compounds as those previously described.

It has been discovered that while some guanine nucleosides having a pyridine or selected other tertiary amine in the 6th position in accordance with the present invention are not stable for long periods of time, they may be nucleophilically substituted by other compounds which are storage stable, in dramatically increased yields. For example, when concentrated aqueous ammonia (which is nucleophilic in and of itself) is added directly to the 6-pyridine substituted guanine nucleoside compositions in accordance with the present invention, a substituted guanine nucleoside having an $NH_2$ group in the 6th position thereof is obtained in yields of about 34%. This is a substantially greater yield than can be obtained through known processes. However, this yield is substantially lower than those obtained through the use of other processes, in accordance with the present invention.

In accordance with another aspect of the present invention there is provided a composition of matter comprising a saccharide and a nitrogenous heterocyclic purine having a compound derived from a mono-, di-, and tri-halogen substituted acetic anhydride bonded thereto in the $N^2$ position. In a particularly preferred embodiment the anhydride is a trifluoroacetic anhydride.

It has been advantageously discovered that guanine nucleosides having specific $N^2$ protecting groups are useful in the formation of 6-substituted guanine nucleosides, even when compared to $N^2$ protecting groups of very similar structure. For example, it was unexpectedly discovered that a 6-substituted pyridyl guanine derivative would be formed having at least one $N^2$ group of $CF_3CO$ under the mild conditions of the processes of the present invention.

As previously discussed, these pyridyl-containing guanine nucleosides may be readily converted to other useful intermediates, such as, for example, 2-N-trifluoroacetamido-6-pentafluorophenoxy-9-(2-deoxy-beta-D-erythro-pentofuranosyl)purine in yields approximating 95% after 24 hours. These intermediates can then be inserted into an oligonucleotide and used as is, or converted while within a nucleotide to other useful forms, or may be converted to other useful 6-substituted nucleosides such as 2,6-diamino-9-(2-deoxy-beta-D-erythro-pentofuranosyl)purine in high yields.

The pyridyl may also be readily converted to the 2,6-diamino-deoxyguanosine directly; however, yields are lower, on the order of 34% in only 1.5 hours.

While not wishing to be bound by any particular theory of operation, the present invention includes the realization of the roles played by substituents in the $N^2$ and 6th positions of a guanine nucleoside in the formation of six substituted derivatives thereof. As the aforementioned Bridson et al. paper clearly indicates, the art has been unable to find the right combination of factors which will allow for the formation of guanine nucleosides and nucleotides substituted in the 6th position with any degree of specificity, versatility, or usefulness. For example, the aforementioned article discloses the ability to convert, by acylation, quanosine to a 6th acyl substituted form. However, it is unable to accomplish anything useful with this compound. The present invention includes the realization that certain highly electron withdrawing acyl groups when reacted to form acyl derivatives in the 6th position can be readily substituted by a pyridyl or pyridinium ion and thereafter further substituted to form useful compounds. Thus, the invention includes a realization of the roles, respectively, of acylation and substitution with a pyridinium ion in the formation of useful 6-substituted guanine nucleosides and nucleotides.

It has also been hypothesized that the presence of a sufficiently electron withdrawing species in the $N^2$ position is necessary for the formation of, for example, the pyridyl or other tertiary amine containing compound. For example, preliminary indications are that use of the processes of the present invention on inosine (a nucleoside having an H bonded to the second position) will not result in the formation of a pyridyl derivative even when such strongly electron withdrawing species as trifluoroacetic anhydride derivatives are used to acylate the 6th position. It appears, therefore, that there are some localized effects which encompasses both the 6th and the $N^2$ position and which allow for the formation of intermediates in accordance with the present invention. Presumably, of course, any acylating agent which is a derivative of a carboxcylic acid or in fact, any electron withdrawing group might be sufficient in the $N^2$ position to allow for the formation of a pyridyl group in the 6th position depending upon the electronegativity of the acylating group used in the 6th position. It has been found, however, that the use of more strongly electronegative substituents in the $N^2$ position will allow for greater flexibility in the groups used to both acylate and substitute in the 6th position. It is preferred therefore, that the $N^2$ group or its corresponding carboxylic acid analog will have an electronegativity greater than that of acetic acid. This means the corresponding acid is more acidic than acetic acid.

Consider, for example, that reactions using a deoxyguanosine having an acetyl group(s) in the $N^2$ position fail to produce readily detectable amounts of the pyridyl derivative even though the reaction mixture was driven for 20 hours at 50° C. Trifluoroacetic anhydride derivatives used to acylate the 6th and the $N^2$ positions, however, produce radically different results, including the formation of a high concentration of the pyridyl derivative.

While these compounds are structurally similar in some respects, (acetic acid and trifluoroacetic acid) they are very different in terms of their electron withdrawing nature and electronegativity. For example, the relative acidity of acetic acid and trifluouroacetic acid are indicators of such electronegativity. Trifluoroacetic acid is considerably more acidic (lower pH, higher in acidity) and has a disassociation constant ($K_a$) of 0.59 while acetic acid has $K_a$ of $1.8 \times 10^{-5}$. In terms of $pK_a$, these values are 0.23 and 4.72, respectively. This indicates that the former (trifluoroacetic acid) is about 33,000 times as acidic as the latter (acetic acid).

Presumably, therefore, an acyl group containing an acylating agent whose corresponding carboxylic acid analog has a $pK_a$ which is lower than that of acetic acid may be useful in accordance with the present invention. Certainly compounds with electronegativities comparable to or greater than that of trifluoroacetic anhydride derivatives will be readily useful. Accordingly, compounds having substituents in the $N^2$ position whose carboxylic acid counterparts have an $pK_a$ less than that of acetic acid are preferred, as is the use of such compounds as acylation agents for the 6th position.

In addition to being relatively efficient to make, the nucleosides produced in accordance with the present invention are useful in that they may be used to generate a wide variety of other useful compounds. For example, these compounds are useful in the production of oligonucleotides in a quick and convenient manner because these $N^2$ protecting groups will be completely cleaved with a high degree of specificity and control.

Furthermore, the compounds of the present invention may be inserted into oligonucleotides in various forms, and thereafter converted into other useful forms. For example, a nucleoside having a pentafluorophenoxy group in the 6th position could first have the saccharide protecting group removed from the 3' and 5' positions of the 2'-deoxyribose by hydrolysis without removing the $N^2$ protecting group. The resulting 6th and $N^2$ position substituted guanine nucleoside can be re-protected in the 3' and 5' positions with protecting groups useful for nucleotide insertion and subsequently inserted into a nucleotide. Thereafter, the phenoxy group in the 6th position could be replaced, for example, with dimethylamino pyridine. This may be accomplished in an environment substantially free from compounds which promote hydrolysis such that the $N^2$ protecting group remains. In the presence of compounds which do promote hydrolysis, the deprotected, 6 substituted derivative is formed. Both of these compounds are fluorescent.

Specifically, there is provided, a process for the modification of an oligonucleotide containing a 6-substituted guanine nucleoside comprising the steps of:

providing an oligonucleotide having a structure of the formula (VI):

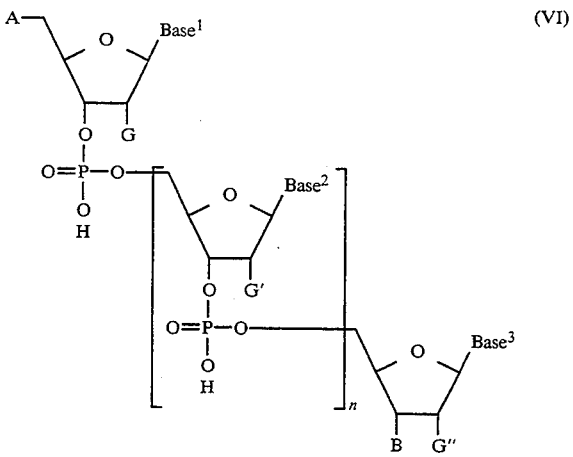

wherein n is 0 or a positive integer, G, G' and G" may be the same or different and comprise hydrogen, hydroxyl, or a protected hydroxyl group, Base1, Base2, and Base3 may be the same or different and comprise a substituted or unsubstituted purine or pyrimidine base, or mixtures thereof, and wherein at least one of said Bases has a structure of the formula (VII):

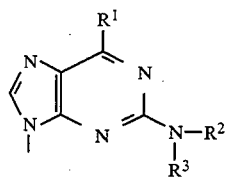

wherein $R^1$ is a nucleophile capable of binding at the 6th position of a purine ring system without cleaving $R^2$; $R^2$ is an electron withdrawing group whose corresponding carboxylic acid has a $pK_a$ less than that of acetic acid; $R^3$ may be the same as or different from $R^2$ and may be an electron withdrawing group or hydrogen, and wherein A comprises a first protecting group, hydroxyl, hydrogen, or a mono-, di-, or tri-phosphate, B comprises a second protecting group, hydroxyl, hydrogen, or a mono-, di-, or tri-phosphate, and A and B may be the same or different; and substituting $R^1$ with a nucleophile.

In accordance with another aspect of the present invention there is provided a 6-dialkylaminopyridinium-9-(2-deoxy-beta-D-erythro-pentofuranosyl)purine. In a preferred embodiment the composition is 6-dimethylaminopyridinium-9-(2-deoxy-beta-D-erythro-pentofuranosyl)purine. The corresponding ribose nucleosides are also provided hereby. These compositions have been found to be particularly useful since they are highly compatible with oligonucleotides and may be readily inserted therein and because they are, in general, fluorescent and therefore useful as labeling compounds. These may be used for replacing radioactive species such as $P^{32}$ which is used in auto radiography (DNA fingerprinting). $P^{32}$ has the disadvantage of a short half-life and radioactivity. The use of fluorescent nucleosides in accordance with the present invention overcomes both problems. Thus the fluorescent species in accordance with the present invention may be used in place of radioactive compounds in other classic diagnostic techniques such as radioimmunoassay and the like.

In accordance with another aspect of the present invention there is provided an oligonucleotide having a structure of the formula (VI):

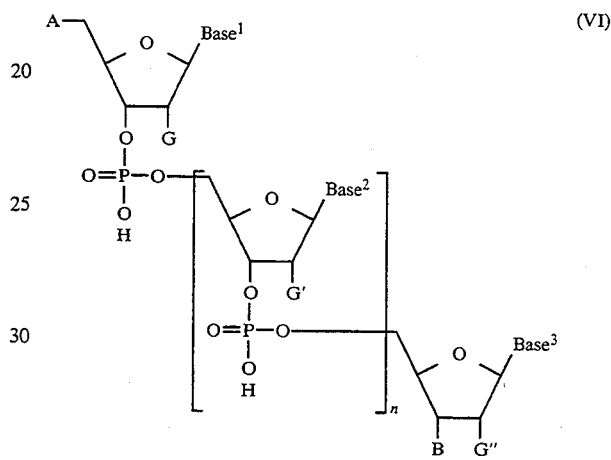

wherein n is 0 or a positive integer, G, G' and G" may be the same or different and comprise H, OH, or a protected hydroxyl group, Base1, Base2, and Base3 may be the same or different and may be a substituted or unsubstituted purine or pyrimidine base, or mixtures thereof, and wherein at least one Base has a structure of the formula (VII):

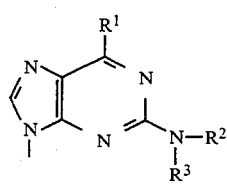

wherein $R^1$ is a nucleophile capable of binding at the 6th position of a purine ring system without cleaving $R^2$; $R^2$ is H or an electron withdrawing group; $R^3$ may be the same as or different from $R^2$ and may be an electron withdrawing group or H; and wherein A comprises a first protecting group, OH, H, or a mono-, di-, or tri-phosphate, B comprises a second protecting group, OH, H, or a mono-, di-, or tri-phosphate, and A and B may be the same or different.

In a preferred embodiment, $R^2$ comprises an acyl portion of a reactive acid derivative whose corresponding carboxylic acid has a $pK_a$ less than that of acetic acid.

These compositions are oligonucleotides which may be useful as DNA probes, as fluorescent labeling compounds, and the like.

In accordance with yet another aspect of the present invention, there are provided processes for the production of 2,6-diamino-9-[saccharide]purine. This includes the production of both substituted guanosine and deoxyguanosine derivatives. One such process comprises the steps of:

acylating at least the 6th position of a guanine nucleoside with an acylating agent;

substituting a pyridinium ion for said acyl group in the 6th position of said nucleoside; and reacting said nucleoside with concentrated aqueous ammonia and forming said 2,6-diamino-9-[saccharide]purine.

In a closely related aspect according to the present invention, there is provided a process of producing 2,6-diamino-9-[saccharide]purine comprising the steps of:

acylating at least the 6th position of a guanine nucleoside with an acylating agent;

substituting a tertiary nitrogen of a tertiary nitrogen-containing compound for said acyl group in the 6th position of said nucleoside;

wherein said step of acylating and said step of substituting are conducted in an environment which is substantially free from compounds which promote hydrolysis; and reacting said nucleoside with concentrated aqueous ammonia and forming said 2,6-diamino-9-[saccharide]purine. This includes both ribose and 2'-deoxyribose containing compounds.

In accordance with a further aspect of the present invention a process is provided for making 2,6-diamino-9-[saccharide]purine comprising the steps of:

reacting a guanine nucleoside with a tertiary amine compound which is a pyridine and an acylating agent to form a first reaction product; and reacting said first reaction product with concentrated aqueous ammonia to form a 2,6-diamino-9-[saccharide]purine.

In accordance with another aspect of the present invention, there is provided a process of producing 2,6-diamino-9-[saccharide]purine comprising the steps of:

reacting a guanine nucleoside with a tertiary amine compound and an acylating agent to form a first reaction product, wherein said reaction is conducted in an environment which is substantially free from compounds which promote hydrolysis; and reacting said first reaction product with aqueous ammonia to form a 2,6-diamino-9-[saccharide]purine.

As with all of the other compounds provided hereby, the ribose and 2'-deoxyribose containing nucleosides are particularly preferred.

The processes of the present invention utilize commercially available starting materials and are highly versatile in that either protected or unprotected guanine nucleosides may be used. Experimental yields of these processes have been approximately 34%, which represents a substantial improvement over the prior procedures, such as that disclosed in the *Tetrahydron* article, supra.

Perhaps the most significant and unexpected feature of the processes according to this aspect of the present invention is the dramatic decrease in the length of time required to produce 2,6-diamino-guanine-nucleosides in accordance with the present invention when compared to the times required for conventional processes. In fact, the time required to obtain significantly higher yields of the 2,6-diamino-guanine-nucleosides according to the present invention may be measured in hours, instead of days. See the *Tetrahedron* article, supra. Thus the processes in accordance with the present invention provide highly versatile protocols for the formation of 2,6-diamino-guanine-nucleosides in a more efficient, more cost effective manner.

In accordance with another aspect of the present invention there is provided a process of producing a guanine nucleoside substituted in the 6th position comprising the steps of:

providing a guanine nucleoside;

acylating at least the 6th position of said guanine nucleoside with an acylating agent;

substituting a tertiary amine group for said acyl group in the 6th position of said guanine nucleoside, wherein said steps of acylating and substituting are conducted in an environment which is substantially free from compounds which promote hydrolysis; and substituting said tertiary amine group with a first nucleophile to form a guanine nucleoside substituted in the 6th position.

In accordance with another aspect of the present invention there is provided a process of producing a guanine nucleoside substituted in the 6th position comprising the steps of:

reacting a guanine nucleoside with a tertiary amine compound and an acylating agent to form a first reaction product wherein said reaction is conducted in an environment which is substantially free from compounds which promote hydrolysis; and reacting said first reaction product with a first nucleophile capable of binding at a 6th position of said guanine nucleoside and forming a guanine nucleoside substituted in the 6th position.

These processes allow for the convenient production of guanine nucleosides substituted in the 6th position from commercially available starting materials. They allow for the use of both protected and unprotected guanine nucleosides, and may be used to form a wide variety of useful intermediate and end products.

For example, the processes hereof may be used for the direct formation of 2,6-diamino-substituted-guanine-nucleosides or compositions having dialkylaminopyridinium or methoxy groups in the 6th position thereof. As previously noted, the diamino compounds are useful as intermediates in the formation of other substituted products as well as being directly useful for studying the structure of DNA and the formation of bonds between polynucleotides.

The 6-methoxyguanine derivatives have been useful in quantifying thermodynamic comparisons of base pairs formed by the carciogenic lesson as was discussed in Gaffney and Jones cited supra.

Furthermore, these highly versatile processes may be used for the formation of six substituted guanine nucleosides having, for example, a 4-nitrophenoxy or, pentafluorophenoxy group bonded thereto. As discussed previously these compositions are useful as intermediates for direct insertion into oligonucleotides.

Processes are also provided for the production of 6-(nitrophenoxy)-9-[saccharide]-purine wherein the nitrophenoxy has a nitro group in the 3, 4 or 5 position comprising the step of reacting a guanine nucleoside having a pyridinium ion in the 6th position thereof with a substituted or unsubstituted nitrophenol having a nitro group in the 3, 4 or 5 position and forming a 6-(nitrophenoxy)-9-[saccharide]purine and 6-(substituted halophenoxy-9[saccharide]purine comprising the step of: reacting a guanine nucleoside having a pyridinium ion in a 6th position thereof with a compound having a structure of the formula (II):

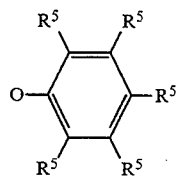

(II)

wherein R⁵ comprises a halogen or hydrogen and wherein at least three R⁵ groups are halogens, and forming a 6-(substituted halo-phenoxy-9-(saccharide)purine.

Also provided hereby is a composition of matter having a structure of the formula (I):

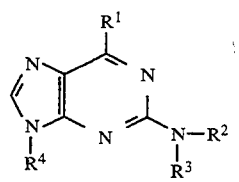

(I)

wherein $R^1$ is a substituted phenoxy group having at least one election withdrawing group attached thereto, with the proviso that if said electron withdrawing group is a halogen, at least three halogens are attached to said phenoxy group, and with the further proviso that the phenoxy group does not contain a substituent at the 2 or 6 position of a size that will create steric hindrance. $R^2$ is an electron withdrawing group, H, a substituted or unsubstituted aliphatic compound having from about 1 to about 20 carbons or a substituted or unsubstituted aromatic compound having from about 1 to about 20 carbons; $R^3$ may be the same as or different from $R^2$ and may be an electron withdrawing group, H, a substituted or unsubstituted aliphatic compound having from about 1 to about 20 carbons, or a substituted or unsubstituted aromatic compound having from about 1 to 20 carbons; and $R^4$ is a substituted or unsubstituted saccharide.

DETAILED DESCRIPTION OF THE PREFERRED EMBODIMENT

Generally, a nucleoside comprises a nitrogenous heterocyclic base which is derived from either a pyrimidine or purine, and a pentose or five-membered sugar. A nucleotide has an additional molecule of phosphoric acid attached to the saccharide. In accordance with the present invention, however, a nucleoside may broadly include a nitrogenous heterocyclic base as previously described attached to a saccharide which may or may not be a pentose. Saccharides include both aldoses (sugars derived from monosaccharides having an empirical formula $(CH_2O)_n$ where n equals 3 or some larger number and the monosaccharide has an aldehyde or like group at the end of its chain) or a ketose (derivatives of monosaccharides having a ketone group within its structure other than at its end). Saccharides also include both the ring and open chain forms and the levorotatory (L) and the dextrorotatory (D) forms and the alpha and the beta forms thereof.

Pentoses include ribose, arabinose, xylose, lyxose, ribulose, and xylulose. Other useful saccharides include hexoses such as allose, altrose, glucose, mannose, gluose, idose, galactose, talose, psicose, fructose, sorbose, and tagatose. Tetroses include erythrose, threose, and erythrulose. Thus, when in this document reference is made to a chemical whose name includes "[saccharide]", or elsewhere where the word saccharide is used it should be understood that the alpha or beta, D or L; and oxy or deoxy forms of saccharides are contemplated. Furthermore, in preferred embodiments according to the present invention, the term "[saccharide]" in a name, or the term saccharide in text both refers to ribose or 2'-deoxyribose.

Purines and pyrimidines are two classes of nitrogenous bases which are generally found in nucleosides and are heterocyclic compounds. The most well known of these compounds are the purines adenine (6-amino purine), guanine (2-amino-6-oxopurine) and the pyrimidines cytosine (4-amino-2-oxopyrimidine), thymine (5-methyl-2,4-dioxopyrimidine) and uracil (2,4-dioxopyrimidine) which are the so called "Watson-Crick" compounds of DNA and RNA. They are also referred to, generically, as bases. Other bases include $N^6$-methyladenine, 2-methylguanine, 5-methylcytosine, 5-hydroxymethylcytosine, psuedo-uridine, inosine, ribothymidine, 5,6-dihydrouridine, 1-methylinosine, 1-methylguanosine, $N^2$-dimethylguanosine, 5,6-dihydrouracil, 1-methyluracil, 3-methyluracil, 5-hydroxymethyluracil, 2thiouracil, $N^4$-acetylcytosine, 3-methylcytosine, 5-methylcytosine, 5-hydroxymethylcytosine, 1-methyladenine, 2-methyladenine, 7-methyladenine, $N^6$-methyladenine, $N^6,N^6$-dimethyladenine, $N^6$-(delta²-isopentenyl)adenine, 1-methylguanine, 7-methylguanine, $N^2$-methylguanine and $N^2,N^2$-dimethylguanine.

In general, the present invention is directed to compounds which are based in part on guanine having a structure of the formula (A)

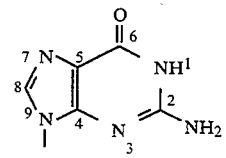

(A)

having an oxo, ketone group in the 6th position and an amine group attached in the 2nd position. Traditionally, guanine is attached to a saccharide at the 9th position to form a nucleoside.

While one aspect of the present invention is primarily directed to compounds in which guanine is attached in the 9th position to a saccharide, it should be understood that guanine may be attached to other compositions without departing from the scope of the present invention. This is particularly true if the group attached to the ninth position is something other than a proton or a group having strong localized electrophilic or nucleophilic properties.

For example, instead of a saccharide, it is envisioned that long or short chain aliphatic and substituted aliphatic groups, as well as aromatic compounds such as benzene, would behave much the same in nucleosides as nucleosides containing saccharides in the 9th position when used in the processes of the present invention. It is possible that where the 9th position contains a proton, reactions may be somewhat different. However, it is anticipated that the processes need only be modified to the extent that additional stoichiometric amounts of acylating agents or other material will be required. Alternatively, it is anticipated that the reaction might preferentially include the use of a protecting group to prevent further reactions in that position.

In accordance with preferred embodiments of the present invention, there is provided a nucleoside which has a structure of the formula (I):

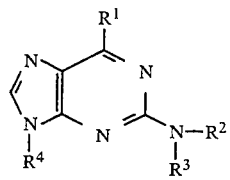

(I)

wherein $R^1$ is an oxo, ketone, or a nucleophile.

A nucleophile in accordance with the present invention is a group which contains an electron rich atom or atoms capable of donating electrons. During different portions of the process of the present invention, the term nucleophile may include those compounds which are capable of bonding at the 6th position of a purine ring system without cleaving $R^2$ or which do not themselves promote hydrolysis. These may include nitrophenoxy groups having a nitro group in the 3, 4 or 5 position or other substituted phenoxy groups. Also included are halogen substituted phenoxy compounds so long as the aggregate of the halogen substitutions is sufficient electronegative or electron withdrawing. When the halogen used is fluorine, two or more fluorine substituents have been found to be required. It is preferred, of course, that the aggregate of the substitutions be as electronegative as possible and to that end, a pentafluoro substituted phenoxy group is amongst the most preferred nucleophiles useful in accordance with the present invention.

When the halogen used is chlorine or another of the less electronegative halogens, three or more will be required.

Phenoxy groups which are substituted in the 3, 4 and/or 5 position are most preferred in accordance with the present invention. This is because substitutions in the 2 and/or 6 position may be of a size sufficient to create steric hindrance which interfere with their ability to react in the processes of the present invention. Therefore, such compounds as ortho- or 2-nitrophenoxy or compound substituted in the 2 and/or 6 position with electron withdrawing species having a greater atomic radii than, for example, chlorine are not preferred, as they will reduce the process efficiency.

Tertiary amines have also been found to be effective as nucleophiles in accordance with the instant invention in that they are capable of bonding to the 6th position without cleaving the $R^2$ group. While primary and secondary amines are chemical analogs to compounds such as alcohols inasmuch as they have both electron donating properties and electron accepting properties, tertiary amines are the chemical analogs of ethers in that both ethers and tertiary amines have only basic, electron donating properties. A tertiary amine is a nitrogen bonded in three positions to carbon or other non-proton based substituents. Tertiary amines include both aromatic compounds such as pyridine or substituted pyridines such as dialkylamino pyridine or dimethylamino pyridine (DMAP), and aliphatic amines including trialkylamines, such as trimethylamine or triethylamine.

Other nucleophiles useful in accordance with the present invention and particularly useful during other portions of the present invention are those which cause hydrolysis of the $R^2$ group in the $N^2$ position, (the $N^2$ protecting group). These include primary amines and ammonia as well as primary alcohols, certain secondary and tertiary alcohols, certain secondary amines, thiols, $H_2S$ and the like. When added, these compositions tend to promoted hydrolysis, particularly of the $N^2$ protecting groups such as $R^2$.

Certain nucleophiles do not, in and of themselves, cause hydrolysis of $R^2$. However, when combined with other compounds such as water, alcohol, or ammonia they may cause hydrolysis. These may, of course, be useful in accordance with the present invention. Consider, for example, that DMAP may be added during the step of substituting a tertiary amine with a first nucleophile. If this substitution is conducted in the presence of compounds which promote hydrolysis, then a 6th substituted substituent would be realized in which protecting groups on a saccharide attached as $R^4$ as well as the groups in positions $R^2$ and $R^3$ would be hydrolyzed to form hydrogen or hydroxide groups. The same group (DMAP), however, may be added in an environment which is substantially free from other compounds which promote hydrolysis. In this eventuality, a DMAP 6 substituted guanosine may be realized wherein at least the $N^2$ protecting group in the $R^2$ position remains.

Secondary amines represent an interesting class of compounds with regard to the present invention in that certain secondary amines will behave more as an electrophile than a nucleophile. To that extent, these compounds will not be useful in accordance with the processes of the present invention. However, those which are more nucleophilic in character as defined above may find application in the processes of the present invention.

Other nucleophiles useful in accordance with the present invention include methylamine, ethylamine, propylamine, butylamine, pentylamine, other primary alkylamines; dimethylamine, diethylamine, dipropylamine, dibutylamine, dipentylamine, other secondary alkylamines; trimethylamine, triethylamine, other tertiary alkylamines; benzylamine, substituted benylamines; pyridine, substituted pyridines, methanol, ethanol, propanol, other primary and secondary alcohols, $H_2S$, methanethiol, other primary and secondary thiols; thiophenol and substituted thiophenols; other aromatic or heterocyclic thiols.

$R^2$ may be hydrogen in the unreacted nucleosides and may be hydrogen again at the conclusion of the processes in accordance with the present invention and/or when placed into a nucleotide or oligonucleotide. $R^2$ may be a substituted or unsubstituted aliphatic compound having from about 1 to about 20 carbons or a substituted or unsubstituted aromatic compound having from about 1 to 20 carbon atoms. $R^2$ may also be an $N^2$ protecting group. For the purposes of the present invention, the term "protecting group" indicates a compound which will inhibit the reaction of a group in the position being protected, but which may be readily removed when desired. The term "$N^2$ protecting group" indicates a group which protects at least one of the positions on the nitrogen attached in the 2nd position to the purine ring. $R^2$ is preferentially, however, an electron withdrawing group and in particular, an electron withdrawing group whose corresponding carboxylic acid has a $pK_a$ less than that of acetic acid. That is to say, compounds whose carboxylic acid analog are stronger acids than acetic acid. More particularly, the $R^2$ group comprises at least the acyl portion of a reactive carboxylic acid derivative and particularly those whose corresponding carboxylic acid have a $pK_a$ as discussed above.

$pK_a$ is the negative log of $K_a$, which is a dissociation constant. $K_a$ may be expressed, based on the equation HA (proton containing acid)+$H_2O$=$H_3O^+$+A (conjugate base), as:

$$K_a = \frac{[H_3O+][A]}{[HA]} \cdot \frac{fH\,fA}{fHA}$$

where [$H_3O+$], [A] and [HA] represent the concentrations of conjugate acid, conjugate base and acid respectively and where fH, fA and fHA are activity coefficients. See Ramette, *Chemical Equilibrium And Analysis*, Addison-Wesley, 1981, 258–260. pH is the negative log of [$H_3O+$].fH.

Carboxylic acids from which anhydrides, esters and acid halides in accordance with the present invention are derived, may include, without limitation, fluoroacetic acid, chloroacetic acid, bromoacetic acid, dichloroacetic acid, trichloroacetic acid, dibromoacetic acid, trichloracetic acid, methoxyacetic acid, cyanoacetic acid, nitroacetic acid, iodoacetic acid, HCOOH, $ClCH_2CH_2COOH$, $C_6H_5COOH$, $H_2C=CHCOOH$ and $C_6H_5CH_2COOH$.

$R^3$ may be the same as or different from $R^2$ and may include hydrogen, or an electron withdrawing group. In a preferred embodiment according to the processes of the present invention, both the $R^2$ and $R^3$ positions contain electron withdrawing groups prior to hydrolysis. However, it is believed that the propensity for compounds in accordance with the present invention to form reaction intermediates in which both $N^2$ positions, namely $R^2$ and $R^3$, are substituted with electron withdrawing species, is somewhat depended upon the stoichiometric amounts of electron withdrawing group added to the reaction mixture, and the amount of steric interference that one group will generate with regard to another.

$R^4$ may be hydrogen, a substituted or unsubstituted aromatic or aliphatic group, or may be a substituted or unsubstituted saccharide as previously described. In preferred embodiments in accordance with the present invention, $R^4$ is a saccharide, and is more preferably a pentose. The most preferred pentoses are the pentoses ribose and 2'-deoxyribose in which the hydroxide group and the 2'-position is replaced by hydrogen. The beta-D forms are also particularly preferred.

In accordance with the present invention, saccharides may be protected at various times by one or more protecting groups. Protecting groups are as defined previously with regard to the $R^2$ group, and are groups which, in the present context, will inhibit the reaction of the saccharide in the position being protected and which may be removed in a controlled fashion by hydrolysis. The list of potential protecting groups is virtually endless so long as the basic functions discussed above are fulfilled. However, in accordance with preferred aspects of the present invention, the following may be considered for use as protecting groups:

$R^6X_2CCOO$—, wherein X comprises hydrogen or a halogen and mixtures thereof, and $R^6$ is an aliphatic group of between about 1 and about 20 carbons or $R^6X_2CCO$— wherein $R^6$ is as above, or halogen substituted or unsubstituted trityl, $(CH_3)_3C(CH_3)_2SiO$—, toluyl, substituted or unsubstituted benzyl, isobutyryl, tert-butyldiarylsilyl, tert-butyldialkylsilyl, $COCH_2CH_2COMe$, bis(diisopropylamino)methoxyphosphine, or compounds having a structure of the formula (III-V).

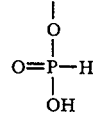

III

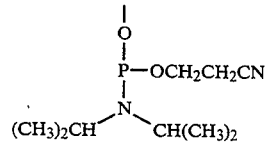

IV

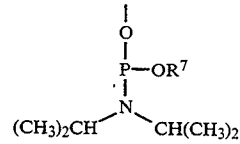

V wherein $R^7$ is a phosphate protecting group.

It should also be noted that certain protecting groups may be used during specific reactions such as those placed in the 3' and 5' position of a ribose and/or 2'-deoxyribose to assist in the facilitation of the attachment of a nucleoside to an oligonucleotide in accordance with the present invention.

In one aspect and one preferred embodiment of processes in accordance with the present invention, saccharide protecting groups may be added to the saccharide prior to the reaction of a nucleoside containing the protected saccharide in accordance with the procedures discussed herein. Thus, a guanine nucleoside may be pre-protected. In that eventuality, the saccharide protecting groups and the $N^2$ protecting groups may be the same or different. In another preferred aspect of the present invention, however, the guanine nucleoside may contain no protecting groups prior to their initial reaction using the processes of the present invention. In that eventuality, and provided sufficient stoichiometric amounts of reactants are used, these saccharides will be protected during acylation by groups which will be the same as the $N^2$ protecting groups. Saccharides would otherwise have an H, OH, or mono-, di-, or triphosphate attached thereto.

Another form of protecting group is the phosphate protecting group which may be found in certain saccharide protecting groups. A phosphate protecting group, like the $N^2$ and saccharide protecting groups, will inhibit a reaction in the position protected. In this case, it will provide protection for the phosphorus found in certain other saccharide protecting groups which are themselves useful for inserting nucleosides into nucleotides. Without limitation, phosphate protecting groups may include methyl and 2-cyanoethyl groups. The trichloroethyl group is also used.

The term acylating agent or acylating compound includes electron withdrawing groups which comprise an acyl portion of a reactive acid derivative. Reactive acid derivatives include substituted aliphatic acids and hydrides, substituted aliphatic acid halides and substituted phenol esters. The most preferred constituents are electron withdrawing groups whose carboxylic acid counterparts have a $pK_a$ less than that of acetic acid. Therefore, the most preferred reactive acid derivatives are those comprising mono-, di-, and tri-halogen substituted acetic anhydrides. The most preferred acylating agent according to the present invention is trifluoroacetic anhydride which yields a trifluoroacetyl in the $N^2$ and 6th positions.

By the term capable of promoting hydrolysis, it is understood that hydrolysis of the $N^2$ groups is contemplated. The fact that hydrolysis of the protecting groups of the saccharide such as those in the 2', 3', or 5' positions of a ribose, and the 3' and 5' positions of a 2'-deoxyribose are hydrolyzed is not of importance. Thus, a reaction conducted in an environment which is substantially free from compounds which promote hydrolysis means an environment free from compounds which will promote hydrolysis in the $N^2$ position. If a pentafluorophenoxy group is used to substitute a pyridinium ion attached in the $R^1$ position in accordance with the processes of the present invention, the fact that, over time, hydrolysis of the saccharide protecting groups occurs, is inconsequential. The pentafluorophenoxy group is not considered as promoting hydrolysis.

An oligonucleotide is a polymeric-like compound wherein a plurality of saccharides are connected by phosphate groups and wherein each individual saccharide has a base or nucleic acid attached thereto. RNA and DNA are forms of oligonucleotides. For the purposes of the present invention, an oligonucleotide may be represented by the formula (VI):

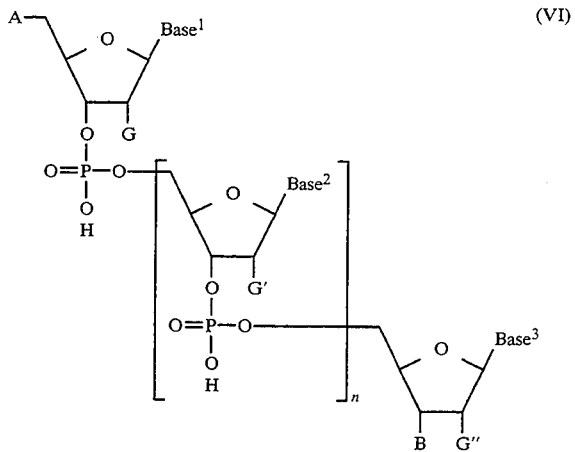

wherein n is 0 or a positive integer, G, G' and G" may be the same or different and comprise hydrogen, hydroxyl, or a protected hydroxyl group, Base1, Base2, and Base3 may be the same or different and comprise a substituted or unsubstituted purine or pyrimidine base, or mixtures thereof, and wherein at least one of said Bases has a structure of the formula (VII):

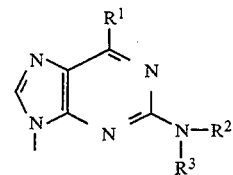

wherein $R^1$ is a nucleophile capable of binding at the 6th position of a purine ring system without cleaving $R^2$; $R^2$ is H or an electron withdrawing group; $R^3$ may be the same as or different from $R^2$ and may be an electron withdrawing group or hydrogen, and wherein A comprises a first protecting group, hydroxyl, hydrogen, or a mono-, di-, or tri-phosphate, B comprises a second protecting group, hydroxyl, hydrogen, or a mono-, di-, or tri-phosphate, and A and B may be the same or different.

It should be emphasized that neither the length of the oligonucleotide nor the order of bases contained therein is of particular importance in accordance with the present invention so long as at least one of the bases is a nucleic acid derivative in accordance with the present invention. It is preferred, however, that oligonucleotides in accordance with the present invention have a length of between about 2 and about 50 repeating units based on the number of nucleic acids contained therein. In a most preferred embodiment according to the present invention, the oligonucleotide is of a size adapted and effective for use as a probe. This generally includes between about 10 and about 20 bases. Oligonucleotides in accordance with the present invention may be produced including nucleosides in accordance with the present invention by any known method. These include, without limitation, the H-phosphonate method and the beta cyanoethyl phosphoromidite method.

The H-phosphonate method is described in Gaffney and Jones, "Large-Scale Oligonucleotide Synthesis By the H-Phosphonate Method" *Tetrahedron Letters*, Vol. 29, No. 22, pp 2619–2122, 1988. Briefly, the pentafluorophenyl derivative of a guanine nucleoside in accordance with the present invention was converted to a 5'-DMT-3'-phosphonate derivative by standard procedures. To summarize one such procedure: the 6-pentafluorophenoxy guanosine of the present invention was first reacted with a slight excess of 4,4'-dimethoxytrityl chloride (DMT-Cl) in pyridine solution (about 5–10 mL per mmol of said pentafluorophenoxy derivative) using a catalytic amount (0.05 eq) of 4-dimethylaminopyridine (DMAP). These are standard conditions, which have been widely published. See for example "Oligonucleotide Synthesis: A Practical Approach" Ed. M. J. Gait, IRL Press, Washington DC, 1984, pp. 23–34. The resulting product was then converted to the H-phosphonate form using the method of Froehler et al. (Froehler, B. C.; Ng, P.G.; Mateucci, M. D. *Nucleic Acids Res.* 1986, 14, 5399–5401) as modified by (Gaffney, B. L.; Jones R. A. *Tetrahedron Lett.* 1988, 22, 2619–2622).

In this procedure, a solution of the above compound is dissolved in methylene chloride (about 10–20 mL per mmol thereof) and was added dropwise to a cooled (ice bath) methylene chloride solution of $PCL_3$, N-methyl morpholine and 1,2,4-triazole in the ratios of 10 mL of $CH_2Cl_2$ per mmol of $PCl_3$, 5 mmol of $PCl_3$, per mmol of the resulting product above, 46 mmol of N-methyl morpholine per mmol of the resulting product above, and 3.3 mmol of triazole per mmol of PCl₃). The remainder of the synthesis and the oligonucleotide synthesis is reported in the above referenced *Tetrahedron Letters* article. The particular oligonucleotide produced was d[TT(PFPG)TT], where d(PFPG) is pentafluorophenyl-2′-deoxyguanosine. This material was then converted to the 2-amino-2′-deoxyadenosine containing molecule d[TT(2-NH2-A)TT] by treatment with concentrated aqueous ammonia for approximately 24 hours.

B-CYANOETHYL PHOSPHORAMIDITE METHOD is reported in Gaffney and Jones, "Thermodynamics of the Base Pairs Formed by the Carcinogenic Lesion O⁶-Methylguanine with Reference both to Watson-Crick Pairs and to Mismatched Pairs" *Biochemistry*, 1989, 28, p 5881. Briefly, the 5′DMT derivative above was reacted with 2-cyanoethyl N,N,N′,N′-tetraisopropylphosphorodiamidite. To summarize its preparation the 5′DMT derivative, dissolved in dry acetonitrile (5 mL per mmol), was treated with tetrazole (0.5 eq), diisopropylamine (0.7 eq), and after five minutes between 1.1 and 1.3 eq of the 2-cyanoethyl N,N,N′,N′-tetraisopropylphosphorodiamidite was added. See A. D. Barone et al., "In situ Activation of Bis-Dialkylphosphines—A New Method for Synthesizing Deoxyoligonucleotides On Polymer Supports," *Nucleic Acids Res.*, 1984, Vol 12, pgs 4051–4061. The product was purified by chromatography. The production of the oligonucleotide may be summarized as follows: 5′-DMT-thymidine bound to controlled pore glass (CPG) was treated sequentially with: 1) 2% dichloroacetic acid (to cleave the DMT group); 2) a solution of 0.16M tetrazole in acetonitrile (20–32 eq) and 0.04M of the 5′-protected cyanoethylphosphoramidite IV′ (5–8 eq) in acetonitrile (coupling); 3) a solution of 0.016M I₂ in 89% tetrahydrofuran (THF), 10% water, and 1% pyridine, for 30 sec (oxidation); 4) a mixture containing 5% DMAP, 5% pyridine, 8% acetic anhydride and 82% THF for 11 sec (capping). This cycle was then repeated using 5′-DMT-thymidine-3′-cyanoethylphosphoramidite in place of the 5′, 3′ protected guanine nucleoside, to give as the final product d[T(PFPG)T]. This compound was converted to d[T(2-NH₂-A)T] by heating in concentrated aqueous ammonia for 24 hours.

After the 6-substituted guanine nucleoside has been inserted into an oligonucleoside, it may be used directly. For example, a nucleoside having a DMAP in the 6th position may be used in as much as the nucleotide is fluorescently labeled. This may include its use in both the N² protected or unprotected form. However, the nucleoside may also be further substituted in the 6th position after the nucleoside has been incorporated in an oligonucleotide. For example, a 6-substituted pentafluorophenoxy guanine nucleotide which is part of an oligonucleotide may be converted to the DMAP species with or without deprotecting the N² position. Alternatively, the nucleotide may be converted to 2,6-diamino compound by reaction with concentrated ammonia.

Specifically there is provided a process for the modification of an oligonucleotide containing a 6-substituted guanine nucleoside comprising the steps of:
providing an oligonucleoside having a structure of the formula (VI):

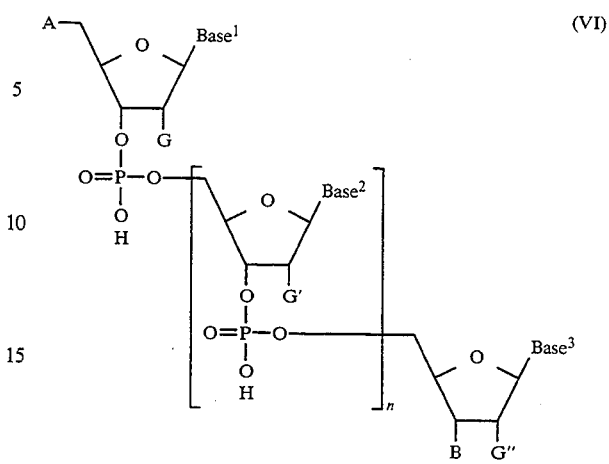

wherein n is 0 or a positive integer, G, G′ and G″ may be the same or different and comprise hydrogen, hydroxyl, or a protected hydroxyl group, Base1, Base2, and Base3 may be the same or different and comprise a substituted or unsubstituted purine or pyrimidine base, or mixtures thereof, and wherein at least one of said Bases has a structure of the formula (VII):

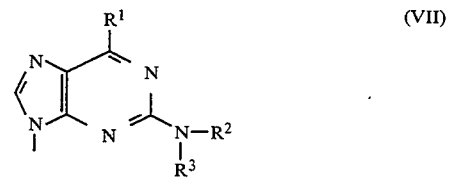

wherein R¹ is a nucleophile capable of binding at the 6th position of a purine ring system without cleaving R²; R² is an electron withdrawing group whose corresponding carboxylic acid has a pK$_a$ less than that of acetic acid; R³ may be the same as or different from R² and may be an electron withdrawing group or hydrogen, and wherein A comprises a first protecting group, hydroxyl, hydrogen, or a mono-, di-, or tri-phosphate, B comprises a second protecting group, hydroxyl, hydrogen, or a mono-, di-, or tri-phosphate, and A and B may be the same or different; and substituting R¹ with a nucleophile.

In one embodiment the step of substituting R¹ may be conducted in the presence of compounds which promote hydrolysis. This includes the use of nucleophiles which themselves cause hydrolysis of the N² protecting group, such as concentrated NH₃, or those nucleophiles which do not, such as DMAP, but which are added in conjunction with other compounds which can cause hydrolysis. Nucleophiles in accordance with this aspect of the present invention include primary, secondary, or tertiary amines, primary alcohols, H₂S, thiols, or concentrated ammonia.

In accordance with another embodiment of this process the step of substituting R¹ with said nucleophile is conducted in an environment which is substantially free from compounds which promote hydrolysis. In this case, nucleophiles useful for substitution into the R¹ position include tertiary amines or a substituted phenoxy having at least one electron withdrawing group attached thereto, with the proviso that if said electron withdrawing group is a halogen, a plurality of halogens are attached to said phenoxy and with the further proviso that said phenoxy does not contain a substituent at the 2 or 6 position of a size that will create steric hindrance. These may include a substituted or unsubstituted nitrophenoxy group in the 3, 4 or 5 position, a non-sterically hindered compound having a structure of the formula (II):

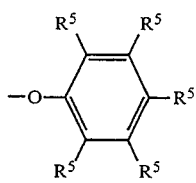

wherein $R^5$ comprises a halogen or hydrogen and wherein at least three of said $R^5$ groups are halogens, or a substituted or unsubstituted tertiary amine.

In either event, it is preferable that the nucleophile be present in an amount effective to completely substitute $R^1$. This may be generally accomplished by the use of a stoichiometric quantity of nucleophile or, more preferably, in excess thereof. Typically, the substitution is also conducted at a temperature above room temperature and at least above 20° C. It is more preferred that the reaction be run at a temperature of greater than 49° C. and most preferably at between about 50° and about 55° C.

In accordance with one aspect of the present invention, processes for producing 2,6-diamino-9-[saccharide]purine are provided. One such process includes the steps of acylating at least the 6th position of a guanine nucleoside with an acylating agent; substituting a pyridinium or pyridyl ion for said acyl group in the 6th position of said nucleoside; and reacting said nucleoside with concentrated aqueous ammonia to form said 2,6-diamino-9-[saccharide]purine.

In accordance with another aspect of the procedure described, a tertiary nitrogen of a tertiary nitrogen containing compound is used to substitute for said acyl group in the 6th position of a nucleoside and the steps of acylating and substituting the guanine nucleoside are conducted in an environment which is substantially free from compounds which promote hydrolysis. These steps are again followed by reacting the nucleoside with concentrated aqueous ammonia to form 2,6-diamino-9-[saccharide]purine. By saccharide, it is understood that preferred saccharides are the beta-D forms of ribose and 2'-deoxyribose.

Those of ordinary skill in the art have assumed that acylation of guanosine and substitution with a pyridinium ion are two incongruous steps. This is evidenced by the Bridson, et al. article discussed in the background section which illustrates that it is possible to acylate the $R^1$ position or the $N^2$ position of a guanine nucleoside, but not both, even when pyridine is present, albeit present as a solvent. Chollet, also referred to in the background section hereof, demonstrates that it is possible to form pyridyl containing nucleosides; however, acylation was not a route contemplated.

The present invention demonstrates, contrary to the teachings of the art, that guanosine may be acylated at least at the 6th position and preferably at at least both the 6th and the $N^2$ positions and thereafter, the acyl group in the 6th position may be selectively substituted with a pyridinium ion formed in situ therewith. The resulting pyridinium/guanine nucleoside complex may then be readily converted to other useful forms, quickly and in high yield or, in accordance with the instant aspect of the present invention, directly converted to the useful 2,6-diamino-9 form by reaction with concentrated aqueous ammonia.

By concentrated aqueous ammonia, it is understood that ammonia having a concentration of 10M or greater is contemplated. Preferentially, commercially available aqueous ammonia solutions having a concentration of 15M may be used. It should be understood, however, that greater concentrations than 15M are also useful. It should be further understood that one having ordinary skill in the art could easily use ammonia concentrations lower than 10M by providing other driving forces such as heat, long periods of exposure, and/or catalysts to drive the reaction, all of which are within the scope of the present invention. Generally, however, solutions of concentration of only 1M will cause hydrolysis of the saccharide protecting groups and may cause hydrolysis of the $N^2$ protecting groups. It is self-evident that ammonia may be considered a compound which in and of itself, provides an environment which promotes hydrolysis.

In a preferred aspect according to the present invention, the acyl group in the 6th position is substituted by a tertiary nitrogen of a tertiary nitrogen-containing compound and preferably pyridine. This includes compounds such as those derived from pyridine, like DMAP. The latter may be particularly useful in that it is fluorescent and may be used as an indication of the degree in which reactions have occurred, etc.

In accordance with another aspect of the present invention, processes of producing 2,6-diamino-9-[saccharide]purine are provided to include the steps of reacting a guanine nucleoside with a tertiary amine compound which is a pyridine and an acylating agent to form a first reaction product and subsequently reacting the first reaction product with concentrated aqueous ammonia to form a 2,6-diamino-9-[saccharide]purine.

More broadly, the process as described may include reacting a guanine nucleoside with a tertiary amine compound and an acylating agent to form a first reaction product wherein said reaction is conducted in an environment which is substantially free from compounds which promote hydrolysis, followed by reaction of the first reaction product with concentrated aqueous ammonia. In a preferred aspect of both of the above-described processes, the tertiary amine compound and the acylating agent are present in an amount effective to completely convert said guanine nucleoside to said first reaction product and the acylating agent is a reactive acid derivative. In accordance with a more preferred embodiment of the present invention, the reactive acid derivative is a substituted aliphatic acid anhydride substituted aliphatic acid halide or substituted phenol ester. More preferred are the reactive acid derivatives of mono-, di-, and tri-halogen substituted acetic anhydrides; and most preferred are the trifluoroacetic anhydride derivatives. However, any reactive acid derivative whose corresponding acid has a $pK_a$ lower than that of acetic acid may be used. It is preferred that the tertiary amine compound be present in an amount of between 3 and 20 ml per mmol of the guanine nucleoside and more preferably, in an amount of between about 5 to 10 ml per mmol of the guanine nucleoside. The reactive acid derivative should be present in an amount of at least 3 mmol per mmol of guanine nucleoside and preferably, between about 3 and about 8 mmol per mmol of said nucleoside.

As is appreciated by the present invention and apparently overlooked by the art, pyridine or other tertiary amine compounds may be used as both solvent as well as reactant. In principle, the amount of pyridine used, for example, can be quite low relative to the amount of guanine nucleoside, but at least the amount of pyridine or other tertiary amine should be a stoichiometric amount. It is hypothesized that acylation using an anhydride produces an ester and an equivalent of acid with each acid molecule protonating a molecule of pyridine or other tertiary amine compounds. Thus, at least stoichiometric amounts of both are required. If the amount of pyridine is drastically reduced, displacement reaction at the 6th position will suffer from a rate reduction as well as a reduction, potentially, in yield.

One molecule of anhydride, which will produce an electron withdrawing group corresponding to a carboxylic acid, having a $pK_a$ lower than that of acetic acid, is required for each sight of acylation. While it may be possible that as little as two molecules of acylating agent will be required for each guanine nucleoside (one each for the 6th and $N^2$ positions), it is likely that acylation of the $N^2$ position occurs at both protons. Thus, the $N^2$ position will be di-acylated at R2 and R3. This is particularly true where the acylating group is of a size that will not interfere sterically with the attachment of a second acyl group. Furthermore, because the processes in accordance with the present invention ideally contain highly electron withdrawing species at both the N2 and 6th positions, it is preferred that the N2 position be di-acylated. Therefore, at least three molecules of reactive acid derivative or acylating agent are preferably used for each mole of guanine nucleoside.

When $R^4$ is ribose and is unprotected in the 2', 3' and 5' positions, additional acylation occurs forming protecting groups at these positions. This requires the equivalence of at least three more molecules of acylating agent per molecule of guanine nucleoside. Additional acylating agent may be present to insure the formation of sufficient pyridyl ions to drive the reaction forward. Thus, it is preferred that an excess of stoichiometric acylating agent and pyridine or other tertiary amine be present. In accordance with a preferred aspect of the process described herein, the saccharides used as $R^4$ are beta-D-ribose and beta-D-2'-deoxyribose. It is also preferred that the reaction be conducted in the presence of a cooling medium such as, for example, an ice bath or cooling jacket. Temperatures of below 23° C. have found to be useful; and particularly, a temperature of 4° C. has been found to be highly preferred optimum.

In addition to the previously described reactions which are primarily useful for the formation of guanine nucleosides having an amino group in the 6th position, similar processes may be used for the formation of 6-substituted guanine nucleosides having a methoxy group in the 6th position.

In accordance with another aspect of the processes of this invention, guanine nucleosides substituted in the 6th position may be produced by providing a guanine nucleoside; acylating at least the 6th position thereof with an acylating agent; substituting a tertiary amine group for said acyl group in the 6th position of the guanine nucleoside, wherein the steps of acylating and substituting are conducted in an environment which is substantially free from compounds which promote hydrolysis; and substituting the tertiary amine group with a first nucleophile. A guanine nucleoside substituted in the 6th position is thus formed.

As discussed previously, the guanine nucleoside provided prior to use of the instant process may be saccharide protected (protected by saccharide protecting groups in all reactive positions on the saccharide, $R^4$). More importantly, however, the guanine nucleoside provided may be protected in at least one $N^2$ position by at least one $N^2$ protecting agent. These include the protecting agents previously discussed.

In accordance with another aspect of the present process, the guanine nucleoside provided may be unprotected in the $N^2$ position as well as in the active sites on the saccharide, $R^4$. In these cases, the process step of acylation will also acylate the $N^2$ and reactive saccharide groups, thus protecting them from further reaction. Acylation occurs as previously described in that the reactive acid derivative, such as, for example, trifluoroacetic anhydride, reacts to form an acid and an ester. The acid protonates one molecule of the tertiary amine and the reactive acid derivative reacts with the oxo group in the 6th position of the guanine nucleoside to form an acyl group, in this case a trifluoroacetyl group. This group is subsequently displaced by the tertiary amine group.

When the compound to be produced is eventually to be used in the production of nucleotides, it is important that the step of acylation and substitution be conducted in an environment which is substantially free from compounds which promote hydrolysis of the $N^2$ protecting group. Otherwise, side reactions will occur which will drastically impact upon the speed and yield of the process of the present invention. Furthermore, reprotection would be required at a later date. The acylating agent should, as in all aspects of the processes of the present invention, be present in an effective amount to completely acylate at least the 6th position of the guanine nucleoside, and the tertiary amine group should be present in an amount effective to completely substitute the acyl group in the 6th position. When unprotected at the $N^2$ position, the amount of acylating agent should be an effective amount to acylate the $N^2$ position as well. If the saccharide is unprotected, the amount of acylating agent should be adjusted accordingly.

Generally, the tertiary amine compound should be present in an amount of between about 3 and about 20 mL per mmol of the guanine nucleoside, and most preferably in an amount of between about 5 to about 10 mL per mmol thereof. The reactive acid derivative from which the acyl group is derived should be present in an amount of at least three mmol per mmol of the guanine nucleoside, and preferably be present in an amount between about 3 and about 8 mmol per mmol of the nucleoside.

Following the steps of acylation and substitution, another substitution step is carried out wherein the tertiary amine group is substituted with a first nucleophile to form a guanine nucleoside substituted in the 6th position. While the guanine nucleoside/tertiary amine group complex is a guanine nucleoside substituted in the 6th position, it is not stable for long periods of time and is not considered to be within the meaning of the term as used herein.

The first nucleophile may be a nucleophile which, in and of itself, provides an environment which promotes hydrolysis. An example of a nucleophile of this type is ammonia. Therefore, the addition of concentrated ammonia at this stage in the process will drive the reaction directly to the formation of guanine nucleosides having an amino group in the 6th position. Yields have been found to be approximately 34% when the process is utilized in this form. The 6-amino-substituted guanine nucleoside would be deprotected in the $N^2$ position in this case.

In accordance with another embodiment of the present invention, a nucleophile may be substituted which does not promote hydrolysis of the $N^2$ position in and of itself, but whose substitution is conducted in the presence of other compounds which will promote hydrolysis. One example of such a substitution is the addition of DMAP accompanied by water, alcohol, or a less concentrated solution of ammonia. This will produce a guanine nucleoside which is deprotected at the $N^2$ position and which is substituted in the 6th position with DMAP.

Alternatively, the first nucleophile may be of a type which does not promote hydrolysis and is added for substitution without the presence of other compounds which will promote hydrolysis. In that eventuality, a $N^2$ protected 6-substituted guanine nucleoside will be produced. Nucleophiles according to this process protocol include tertiary amines, substituted phenoxy compounds having at least one electron withdrawing group attached thereto with the proviso that, if said electron withdrawing group is a halogen, a plurality of halogens are attached to said phenoxy group, and with the further proviso that the phenoxy does not contain a substituent at the 2 or 6 position of a size that will create steric hindrance.

In accordance with a preferred aspect of this protocol, the first nucleophile comprises a substituted or unsubstituted nitrophenoxy group having a nitro group in the 3, 4 or 5 position, a non-sterically hindered compound having a structure of the formula (II):

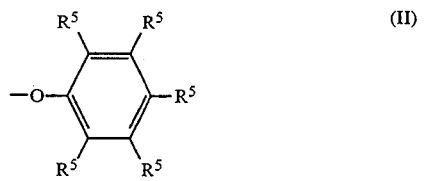

wherein $R^5$ comprises a halogen or hydrogen and wherein at least three $R^5$ groups are halogens, or a tertiary amine such as DMAP or other dialkylaminopyridine.

These compounds are storage-stable and may be separated, purified and stored for later use. One such use involves the subsequent substitution of the nucleophile in the 6th position with a second nucleophile. Such a substitution may be accomplished in the absence of compounds which will promote hydrolysis in which case compounds with different 6-substitutions but which are protected in the $N^2$ position may be realized. For example, a compound having a pentafluorophenoxy group in the 6th position may be substituted with a second nucleophile, such as a 4-nitrophenoxy group, to produce a 4-nitrophenoxy substituted guanine nucleoside. This nucleoside may then be protected in, for example, the 3' and 5' positions of a ribose or deoxyribose attached as $R^4$ and inserted into RNA or DNA, respectively.

Furthermore, the substitution of the first nucleophile with the second nucleophile may be accomplished either in the presence of compounds which do promote hydrolysis or by using compounds which themselves promote hydrolysis. In this eventuality, 6-substituted guanine nucleosides which are deprotected in the $N^2$ position are realized, such as, 2,6-diamino-9-[saccharide]purine or 2-amino,6-methoxy-9-[saccharide]purine. These "second nucleophiles" may therefore comprise primary, secondary or tertiary amines, primary alcohols, $H_2S$, thiols, $NH_3$ (concentrated) or any of the first nucleophiles identified above. These compounds may thereafter be purified.

Thus, the process of the present invention is highly versatile and provides a plurality of routes to accomplish realization of the same compounds. It should be noted, however, that the yields of, for example, the 2,6-diamino-9-[saccharide]purine are dramatically superior when using the two-step nucleophilic substitution of a first nucleophile and a second nucleophile when compared to the more direct tertiary amine displacement. In fact, yields may be quantitative.

In accordance with another aspect of the process of the present invention, a guanine nucleoside substituted in the 6th position may be produced by the steps of reacting a guanine nucleoside with a tertiary amine compound and an acylating agent to form a first reaction product wherein said reaction is conducted in an environment which is substantially free from compounds which promote hydrolysis; and thereafter reacting the first reaction product with a first nucleophile capable of binding at the 6th position of the guanine nucleoside. A guanine nucleoside substituted in the 6th position is thus formed. This 6th position substituted guanine nucleoside may be further reacted with a second nucleophile as previously described.

In accordance with this process the guanine nucleoside may be provided in an $N^2$ protected form or an unprotected form. If the guanine nucleoside is protected, then that amount of tertiary amine compound useful in accordance with this aspect of the present invention is preferably between about 2 and about 20 mL per mmol of the nucleoside and the acylating agent is preferably present in an amount of between about 1 and about 6 mmol per mmol of the guanine nucleoside.

When the guanine nucleoside is unprotected prior to being reacted with the tertiary amine compound and the acylating agent, the amount of tertiary amine compound present in the reaction is preferably between about 2 and about 20 mL per mmol of the guanine nucleoside and the acylating agent should be present in an amount of at least about 3 mmol per mmol of said guanine nucleoside. In a more preferred embodiment in accordance with this process, the tertiary amine compound should be present in an amount of between about 5 and about 10 mL per mmol of guanine nucleoside and said acylating agent should be present in an amount of between about 3 and about 8 mmol per mmol of said guanine nucleoside. The processes of the present invention, as noted before, are preferentially conducted in the presence of a cooling medium and are preferably conducted at a temperature below about 23° C., and most preferably at a temperature of about 4° C.

Finally, a process for producing 6-(nitrophenoxy)9-[saccharide]purine wherein said nitrophenoxy has a nitro group in the 3, 4 or 5 position includes the steps of reacting a guanine nucleoside having a pyridinium ion or other tertiary amine compound in the 6th position thereof with a substituted or unsubstituted nitrophenol having a nitro group in the 3, 4 or 5 position. The process of producing a 6-(substituted)halo-phenoxy-9-[saccharide]purine is also provided comprising the step of reacting a guanine nucleoside having a pyridinium ion or other tertiary amine in a 6th position thereof with a non-sterically hindered compound having a structure of the formula of (II):

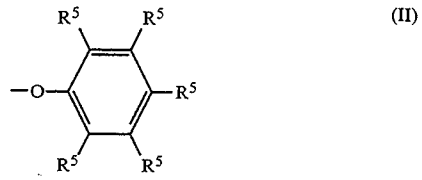

wherein $R^5$ comprises a halogen or hydrogen and wherein at least three $R^5$ groups are halogens.

As will be readily appreciated by one of ordinary skill in the appropriate art, the various 6-substituted nucleosides may be separated from their respective reaction mixtures and purified by any number of conventional means such as those discussed in the references cited herein and in the examples which follow. One preferred method of purification includes neutralization of remaining acid species followed by evaporation, with the residue later being dissolved in water and purified by reversed-phase high pressure liquid chromatography (HPLC) using a gradient elution of from 2 to 5% acetonitrile in water. Other separation techniques exclude the use of neutralizing material and merely include the steps of evaporation of the product to dryness and redissolving the residue in water followed by filtering and washing.

The foregoing will be better understood with reference to the following examples. These examples are for the purposes of illustration. They are not to be considered limiting as to the scope and nature of the present invention.

EXAMPLE I

Production of 2-amino-6-methoxy-9-(2-deoxy-Beta-D-erythro-pentofuranosyl)purine.

To 2 mmol of deoxyguanosine, dried by evaporation of pyridine and suspended in 10 mL of dry pyridine was added dropwise 2.3 mL (16 mmol) of trifluoroacetic anhydride, with cooling in an ice both. After ten minutes a suspension of 4.3 g of sodium methoxide in 300 mL of methanol was added dropwise. After a further 24 hrs, the mixture was treated with a solution of pyridine hydrochloride (12 mL of pyridine/4 mL conc HCl). The excess acid was destroyed by addition of 2 g of sodium bicarbonate and the mixture was evaporated to dryness. The residue was dissolved in water and purified on a Dynamax reversed-phase hplc column using a gradient of 2–5% acetonitrile in water in 45 min at a flow rate of 6 mL/min. Evaporation of appropriate fractions gave 0.36 g (60%) of pure 2-amino-6-methoxy-9-(2-deoxy-Beta-D-erythro-pentofuranosyl)purine. A crystalline sample was obtained by crystallization from water, mp 155°–7°. UV$_{max}$ (MeOH) 281 nm; UV$_{min}$ 281 nm; $^1$H NMR (DMSO-d$_6$) delta (ppm) 8.07 (s, 1,H$_8$), 6.43 (br s, 2, NH$^2$), 6.20("t", 1, J$_{app}$=6.9 Hz, H$_1$'), 5.27 (d, 1, J=3.8 Hz, 3'-OH), 4.98 (t, 1, J=5.5 Hz, 5'-OH), 4.35 (m,1,H$_3$'), 4.00 (s, 3, OCH$_3$), 3.82 (m, 1, H$_4$'), 3.53 (m, 2, H$_{5',5'}$), 2.57 & 2.22 (m & m, 1 & 1, H$_{2'}$& H$_{2''}$). Anal. Calcd. for C$_{11}$H$_{15}$N$_5$O$_4$·H$_2$O: C, 44.15; H, 5.72; N, 23.40. Found: C, 44.15; H, 5.83; N, 23.43.

EXAMPLE II

Production of 2-amino-6-methoxy-9-[2-deoxy-3,5-bis-O-(tert-butyldimethylsilyl)-Beta-D-erythro-pentofuranosyl]purine).

To 6 mmol of 3',5'-bis-tert-butyldimethylsilyl-deoxyguanosine, dried by evaporation of pyridine and dissolved in 60 mL of dry pyridine was added dropwise 3.0 mL (21 mmol) of trifluoroacetic anhydride, with cooling in an ice bath. After stirring for 15 minutes a suspension of 5.7 gm of sodium methoxide in 610 mL of methanol was added in portions. After a further 20 hrs the reaction mixture was poured into 500 mL of water. The mixture was partitioned using four 200 mL portions of petroleum ether. The combined organic layers were evaporated, traces of pyridine were removed by evaporation of toluene and the resulting foam was dissolved in 50 mL of petroleum ether and placed in the cold. Crystallization gave, after filtration, 2.4 gm (80%) of 2-amino-6-methoxy-9-[2-deoxy-3,5-bis-O-(tert-butyldimethylsilyl)-Beta-D-erythro-pentofuranosyl]purine) mp 101°–105° d. UV$_{max}$ (MeOH) 250 nm, UV$_{min}$ 283 nm; $^1$H NMR (CDCI$_3$) delta (ppm) 7.90 (s, 1, H$_8$), 6.30 ("t", 1, J$_{app}$=6.6 Hz, H$_1$'), 4.81 (s, 2, NH$_2$), 4.57 (m, 1, H$_3$'), 4.01 (s, 3, OCH$_3$), 3.96 (m, 1, H$_4$'), 3.77 (m, 2 , H$_{5',5''}$), 2.55 & 2.38 (m & m, 1 & 1, H$_{2'}$& H$_{2''}$), 0.89 & 0.06 (m & m, 9 & 9, Me$_3$CSi). Anal. Calcd. for C$_{23}$H$_{43}$N$_5$Si$_2$O$_4$: C, 54.18; H, 8.50; N, 13.73; Si, 11.01. Found: C, 54.05; H, 8.63; N, 13.80; Si, 10.69.

EXAMPLE III

Production of 2-amino-6-ethoxy-9-[2-deoxy-3,5-bid-O-(tert-butyldimethyslsiyl)-Beta-D-erythro-pentofuranosyl]purine).

To 2 mmol of 3',5'-bis-tert-dimethylsilyldeoxyguonosine, dried by evaporation of pyridine and suspended in 50 mL of dry pyridine was added dropwise 1.0 mL (7mmol) of trifluoroacetic anhydride, with cooling in an ice bath. After 15 minutes a solution of 2.3 gm of sodium ethoxide in 1.75 L of absolute ethanol was added in portions. After a further 60 hours the mixture was concentrated to about 800 mL and poured into 600 mL of cold water. The mixture was filtered and partitioned using five 200 mL portions of petroleum ether. Crystallization from petroleum ether as described above for 6a, gave 540 mg (51%) of 2-amino-6-ethoxy-9-[2-deoxy-3,5-bid-O-(tert-butyldimethyslsilyl)-Beta-D-erythro-pentofuranosyl]purine, mp 120°–124° d. UV$_{max}$ (MeOH) 250 nm, UV$_{min}$ 283 nm; $^1$H NMR (CDCI$_3$) delta (ppm) 7.9(s, 1, H$_8$), 6.33 ("t", 1, J$_{app}$=6.6 Hz, H$_1$'), 4.80 (s, 2, NH$_2$), 4.59 (m, 1, H$_3$'), 4.54 (q, 2, J=7, CH$_2$), 3.87 (m, 1, H$_4$'), 3.79 (m, 2, H$_{5',5''}$), 1.46 (t, 3, CH$_3$), 2.55 & 2.38 (m & m, 1 & 1, H$_{2'}$& H$_{2'}$), 0.91 & 0.06 (m & m, 9 & 9, Me$_3$CSi) . Anal. Calcd. for C$_{24}$H$_{45}$N$_5$Si$_2$O$_4$: C, 55.03; H, 8.65; N, 13.36. Found: C, 54.97; H, 8.83; N, 13.36.

EXAMPLE IV

Production of 2,6-diamino-9-(2-deoxy-Beta-D-erythro-pentofuranosyl)purine.

To 2 mmol of deoxyguanosine, dried by evaporation of pyridine and suspended in 20 mL of dry pyridine was added dropwise 2.3 mL (16 mmol) of trifluoroacetic anhydride, with cooling in an ice bath. After ten minutes 20 mL of cold, concentrated aqueous ammonia was added. After a further 1½ hours the mixture was evaporated to dryness, the residue dissolved in water and the solution filtered through a 100 mL portion of Bio Rad AG 1-X2, hydroxide from resin to remove colored impurities. The resin was washed with 40% methanol in water to elute crude 2,6-diamino-9-(2-deoxy-Beta-D-erythro-pentofuranosyl)purine, which was further purified on the reversed-phase column described above using a gradient of 2–15% acetonitrile in water. Evaporation of appropriate fractions gave 192 mg (34%) of 2,6-diamino-9-(2-deoxy-D-erythro-pentofuranosyl)purine, a sample crystallized from water gave a mp of 148°. $UV_{max}$ (MeOH) 282 nm, $UV_{min}$ 256 nm; $^1$H NMR (DMSO-$d_6$) delta (ppm) 7.91 (s, 1,H$_8$), 6.73 (br s, 2, NH$_2$), 6.17 ("t", 1, $J_{app}$=6 Hz, H$_{1'}$), 5.73 (br s, 2, NH$_2$), 5.25 (m, 2, 3'-OH & 5'-OH), 4.35 (m, 1, H$_{4'}$), 3.54 (m, 2, H$_{5',5''}$), 2.59 & 2.17 (m & m, 1 & 1, H$_{2'}$ & H$_{2''}$). Anal. Calcd. for $C_{10}H_{14}N_6O_3 \cdot H_2O$: C, 42.25; H, 5.67; N, 29,56. Found: C, 42.54; H, 5.33; N, 29.56.

EXAMPLE V

Production of 2-N-trifluoroacetamido-6-(4-nitrophenoxy)-9-(2-deoxy-Beta-D-erythro-pentofuranosyl)purine.

To 4 mmol of deoxyguanosine, dried by evaporation of pyridine and suspended in 60 mL of dry pyridine was added dropwise 3.4 mL (24 mmol) of trifluoroacetic anhydride, with cooling in an ice bath. After 15 minutes a solution of 11.1 g (80 mmol) of 4-nitrophenol in 200 mL of pyridine was added. After a further 48 hours the mixture was concentrated to about 150 mL and poured into 600 mL of water. The mixture was partitioned using four 200 mL portions of ethyl acetate. The combined organic layers were backwashed with three 50 mL portions of water, concentrated to about 15 mL, toluene was added and the mixture was concentrated to a gum which was dissolved in ethyl acetate, filtered and added dropwise to a 400 mL portion of toluene. Filtration and washing with petroleum ether gave 1.3 g (67%) of 2-N-trifluoroacetamido-6-(4-nitrophenoxy)-9-(2-deoxy-Beta-D-erythro-pentofuranosyl)purine.

$UV_{max}$ (MeOH) 271; $^1$H NMR (DMSO-$d_6$) delta (ppm) 12.12 (br s, 1, NH), 8.72 (s, 1,H$_8$), 8.34 & 7.69 (dd, 4, J=9.1 Hz, $C_6H_4NO_2$), 6.41 ("t", 1, $J_{app}$=6.7 Hz, H$_{1'}$), 5.35 (d, 1, J=4.2 Hz, 3'-OH), 4.91 (t, 1, J=5.5 Hz, 5'-OH), 4.50 (m, 1, H$_{3'}$), 3.88 (m, 1, H$_{4'}$), 3.57 (m, 2, H$_{5',5''}$), 2.78 & 2.40 (m & m, 1 & 1, H$_{2'}$ & H$_{2''}$). Anal. Calcd. for $C_{18}H_{15}N_6F_3O_7$: C, 44.63; H, 3.12; N, 17.35; F, 11.77. Found: C, 44.80; H, 3.13; N, 17.20; F, 11.30.

EXAMPLE VI

Production of 2-N-trifluoroacetamido-6-pentafluorophenoxy-9-(2-deoxy-Beta-D-erythro-pentofuranosyl)purine.

To 4 mmol of deoxyguanosine, dried by evaporation of pyridine and suspended in 60 mL of dry pyridine was added dropwise 3.4 mL (24 mmol) of trifluoroacetic anhydride, with cooling in an ice bath. After 15 minutes a solution of 9.6 g (52 mmol) of pentafluorophenol in 200 mL of pyridine was added. After a further 24 hrs the mixture was concentrated to about 150 mL and poured into 500 mL of water. The mixture was partitioned using four 200 mL portions of ethyl acetate. The combined organic layers were washed with three 50 mL portions of water, concentrated to a gum, which was dissolved in about 15 mL of ethyl acetate, and the product precipitated by dropwise addition of this solution to 700 mL of petroleum ether. Filtration gave 2.0 g (95%) of 2-N-trifluoroacetamido-6-pentafluorophenoxy-9-(2-deoxy-Beta-D-erythro-pentofuranosyl)purine. An analytical sample of 2-N-trifluoroacetamido-6-pentafluorophenoxy-9-(2-deoxy-Beta-D-erythro-pentofuranosyl)purine was obtained by treatment with carbon and reprecipitation. $UV_{max}$ (MeOH) 268 nm; $^1$H NMR (DMSO-$d_6$) delta (ppm) 12.1 (br s, 1, NH), 8.80 (s, 1,H$_8$), 6.42 ("t", 1, $J_{app}$=6.7 Hz, H$_{1'}$), 5.38 (m, 1, 3'-OH), 4.90 (m, 1, 5'-OH), 4.20 (m, 1, H$_{3'}$), 3.90 (m, 1, H$_{4'}$), 3.55 (m, 2, H$_{5',5''}$), 2.80 & 2.38 (m & m, 1 & 1, H$_{2'}$ & H$_{2''}$). Anal. Calcd. for $C_{18}H_{11}N_5F_8O_5 \cdot \frac{3}{4} H_2O$: C, 39.83; N, 12.90; F, 28.00. Found: C, 39.38; H, 2.03; N, 12.60; F, 25.56.

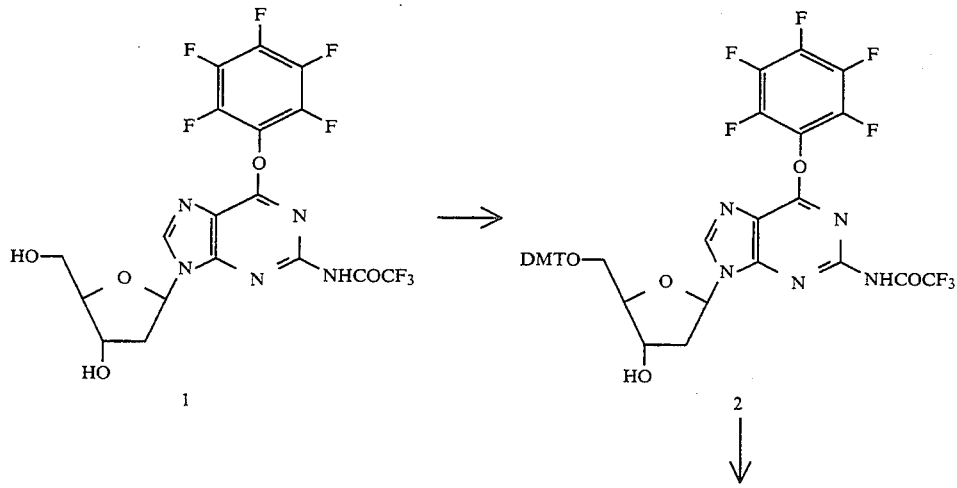

Formula (B)

-continued

Formula (B)

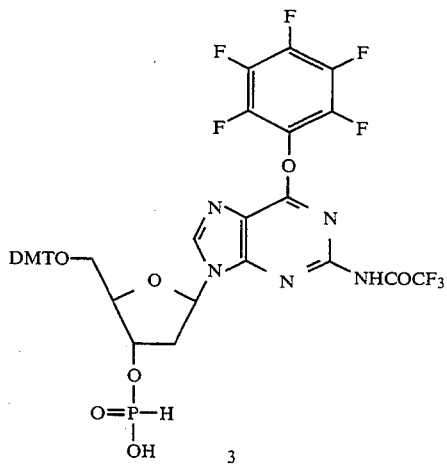

EXAMPLE VII
(H-Phosphonate Method)

With reference to the above formula (B), the pentafluorophenyl 6-substitued guanine nucleoside 1 was converted to the 5'-DMT-3'-phosphonate derivative 3 by standard procedures as follows: 1 was first reacted with a slight excess of 4,4'-dimethoxytrityl chloride (DMT-Cl) in pyridine solution (about 5–10 mL per mmol of 1) using a catalytic amount (0.05 eq) of 4-dimethylaminopyridine (DMAP). This resulted in a 5'DMT-6-pentafluorophenoxy-guanine nucleoside 2. A solution of 2 dissolved in methylene chloride (about 10–20 mL per mmol2) was added dropwise to a cooled (ice bath) methylene chloride solution of $PCL_3$, N-methyl morpholine and 1,2,4-triazole in the ratios of 10 mL of $CH_2Cl_2$ per mmol of $PCL_3$, 5 mmol of $PCl_3$, per mmol of 2, 46 mmol of N-methyl morpholine per mmol of 2, and 3.3 mmol of triazole per mmol of $PCl_3$). This resulted in the formation of 5'DMT-3'-phosphonate-6-pentafluorophenoxy-guanine nucleoside, 3. An oligonucleotide was then prepared using 3 which had a sequence of d[TT(PFPG)TT], where d(PFPG) is pentafluorophenyl-2'-deoxyguanosine by the following protocol:

1. Wash, $CH_2Cl_2$: 20 sec wash, 10 sec wait, repeat 7 times.
2. Deblock, 2.5% dichloroacetic acid, purines: 20 sec acid, 10 sec wait, 40 sec acid; pyrimidines: 20 sec acid, 20 sec wait, then 10 sec acid, 40 sec wait, repeat last two steps three times.
3. Wash, $CH_2Cl_2$: 50 sec.
4. Wash, pyridine/$CH_3CN$ (1/1): 20 sec wash, 10 sec wait, repeat five times.
5. Couple: 0.5 sec 15 mM H-phosphonate, 0.5 sec 75 mM or 0.3 sec 125 mM pivaloyl chloride, repeat as described.
6. Wash, pyridine/$CH_3CN$ (1/1): 20 sec wash, 10 sec wait, repeat five times.
7. Deblock, or repeat from step 1 until completed, or cap: 0.5 sec 50 mM 4, 0.5 sec 250 mM pivaloyl ts chloride, repeat 179 times, wash as step 4, then repeat from step 1 until completed.
8. Oxidize: 0.5 sec 0.4M $I_2$ in THF, 0.5 sec pyridine/N-methylimidazole/water/THF (10/2/10/78), 40 sec wait, repeat 30 times; 0.5 sec 0.4M $I_2$ in THF, 0.5 sec triethylamine/water/THF (10/10/80), 40 sec wait, repeat 30 times.
9. Removal from CPG: The CPG was treated with 1.0M aqueous ammonia for 12 hours at room temperature, filtered and concentrated.
10. The compound is heated in concentrated ammonia for about 24 hours to form the 2,6-diamino derivative

EXAMPLE VIII

Using the procedure of Example VII above up through Step 9, other substituted oligonucleotides may be formed by reaction of the PFPG residue(s) with the other nucleophiles indicated above. For example, heating at 55° with an aqueous solution containing excess DMAP for 48 hours brings about formation of the fluorescent 6-DMAP labeled oligonucleotide, while similar treatment with an ethanolic solution of NaSH or sodium thiophenoxide gives the corresponding 6-S derivatized molecules.

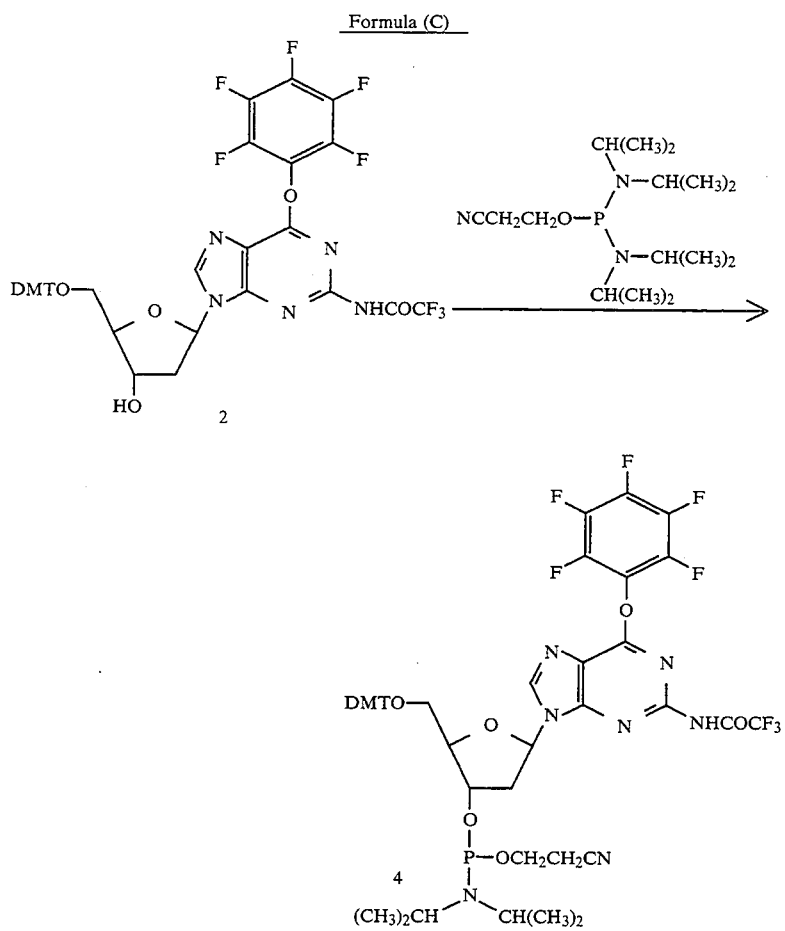

EXAMPLE IX

Beta-Cyanoethyl Phosphoramidite Method.

With reference to the above formula (C) 2-cyanoethyl N,N,N',N'-tetraisopropylphosphorodiamidite is first produced by the following procedure:

To 61 mL of freshly distilled phosphorus trichloride (0.70 mol) dissolved in 300 mL of anhydrous diethyl ether (previously dried over molecular sieves), which was stirred mechanically under a $N_2$ atmosphere and maintained at $-30°$ C., was added dropwise over 2 hours a mixture of 57 mL (0.70 mol) of pyridine, 48 mL (0.70 mol) of freshly distilled 3-hydroxypropionitrile, and 50 mL of anhydrous diethyl ether. The cooling bath was removed, and the mixture was stirred for 18 hours under a small positive $N_2$ pressure. The ether solution was transferred under $N_2$ pressure with filtration into a dry flask. The remaining pyridinium hydrochloride was washed twice with 100-mL portions of anhydrous diethyl ether which was transferred as above. The solution was concentrated on a rotary evaporator, and the resulting liquid was distilled under vacuum (500–1000 mT) with a falling-film distillation apparatus with refluxing ethyl acetate as the heat source to give 70 g (0.41 mol, 58%) of 2-cyanoethyl dichlorophosphite. The $^{31}P$ NMR ($CDCl_3$) showed a single peak at 178.8 ppm (reference 85% $H_3PO_4$).

To 28 g (163 mmol) of this compound dissolved in 300 mL of anhydrous diethyl ether and stirred under $N_2$ at $-20°$ C. was added dropwise 96 mL (685 mmol, 4.2 equiv) of diisopropylamine. The ice bath was removed, and the mixture was stirred for 1 h. The ether solution was transferred with filtration under $N_2$ pressure to a dry flask. The remaining salt was washed twice with 70-mL portions of anhydrous ether which was transferred as above. The solution was concentrated on a rotary evaporator and filtered into a small, dry flask. The liquid was stirred under vacuum for 20 min and then distilled under vacuum (400–500 mT) with the falling-film distillation apparatus with refluxing toluene as the heat source to give 18.5 g (61 mmol, 37% yield) of clear, colorless product. The $^{31}P$ NMR ($CDCl_3$) spectrum showed a single peak at 123.6 ppm (reference 85% $H_3PO_4$).

Compound 2 from Example VII, (5-DMT-6-pentafluorophenoxy-guanine-nucleoside) was then reacted with the 2-cyanoethyl N,N,N',N'-tetraisopropylphosphorodiamidite prepared above. Specifically, nucleoside 2, dissolved in dry acetonitrile (5 mL per mmol), was treated with tetrazole (5 eq), diisopropylamine (7 eq), and after five minutes between 1.1 and 1.3 eq of the 2-cyanoethyl N,N,N',N'-tetraisopropylphosphorodiamidite was added. Product was purified by the following procedure:

After 1 hour, the mixture was partitioned between 200 mL of 5% aqueous $NaHCO_3$ and 200 mL of methylene chloride. The organic layer was washed with a 100-mL portion of water and was then concentrated to a gum. The crude product was purified by flash chromatography on silica gel using a step gradient of 10–25% ethyl acetate in methylene chloride. The appropriate fractions were combined and evaporated to a solid foam. This resulted in the production of a guanine nucleoside protected in both the 5' and 3' positions, nucleoside 4.

An oligonucleotide was then produced by the following protocol:

5'-DMT-thymidine bound to controlled pore glass (CPG) was treated sequentially with: 1) 2% dichloroacetic acid to cleave the DMT group; 2) a solution of 0.16M tetrazole in acetonitrile (20–32 eq) and 0.04M of nucleoside 4 (5–8 eq) in acetonitrile (coupling); 3) a solution of 0.016M of $I_2$ in 89% tetrahydrofuran (THF), 10% water, and 1% pyridine, for 30 sec. (oxidation); 4) a mixture containing 5% DMAP, 5% pyridine, 8% acetic anhydride and 82% THF for 11 sec. (capping). This cycle was then repeated using 5'-DMT-thymidine-3'-phosphonate in place of nucleoside 4, to give as the final product d[T(PFPG)T]. This compound was converted to d[T(2-NH$_2$-A)T] by heating in concentrated aqueous ammonia for 24–48 hours.

EXAMPLE X

Synthesis of 2-amino-6-(4-dimethylaminopyridyl)-9-(2-deoxy-beta-D-erythro-pentofuranoxsyl)purine.

To 2-N-trifluoroacetamido-6-pentafluorophenoxy-9-(2deoxy-beta-D-erythro-pentofuranosyl)purine dissolved in water or aqueous pyridine was added excess 4-dimethylaminopyridine and the mixture was heated at about 50° for one hour to give quantitative conversion to the product.

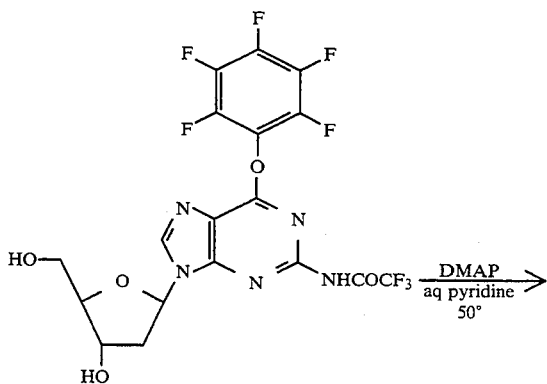

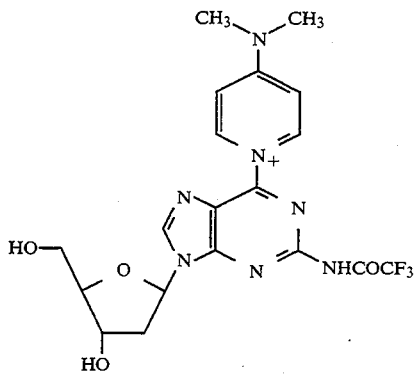

EXAMPLE XI

Synthesis of 6-thio-2'deoxyguanosine.

To 2-N-trifluoroacetamido-6-pentafluorophenoxy-9-(2-deoxy-beta-D-erythro-pentofuranoxsyl)purine dissolved in ethanol was added excess sodium hydrogen sulfide. After heating at reflux for 2–6 hours, conversion to the product was complete.

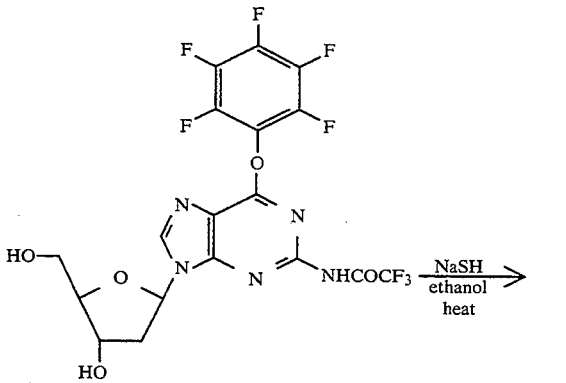

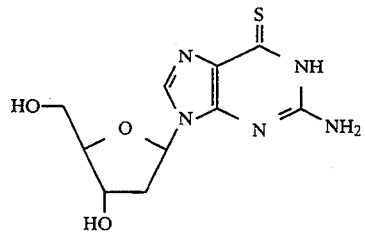

EXAMPLE XII

Synthesis of 6-phenylthio-2'-deoxyguanosine.

To 2-N-trifluoracetamido-t-pentafluorophenoxy-9-(2-deoxy-beta-D-erythro-pentofuranoxsyl)purine dissolved in ethanol was added excess thiophenol and base, such that the number of mmol of base was less than the number of mmol of thiophenol. After heating at reflux for 2–6 hours, conversion to the product was complete.

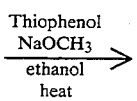

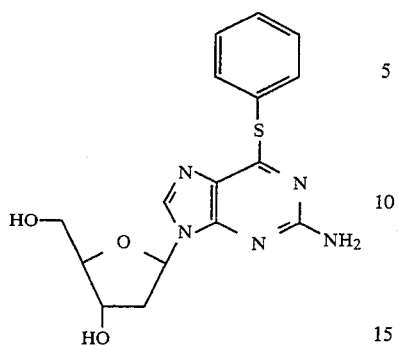
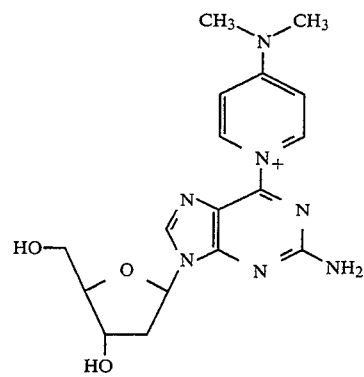

EXAMPLE XIII

Synthesis of N⁶-benzyl-2'-deoxyguanosine.

The 2-amino-6-(4-dimethylaminopyridyl)-9-(2-deoxy-beta-D-erythro-pentofuranoxsyl)purine was suspended in excess benzylamine and heated at 50° for 20 hours to give complete conversion to the product.

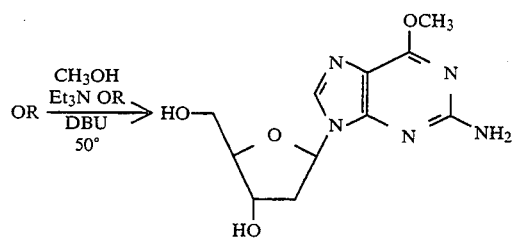

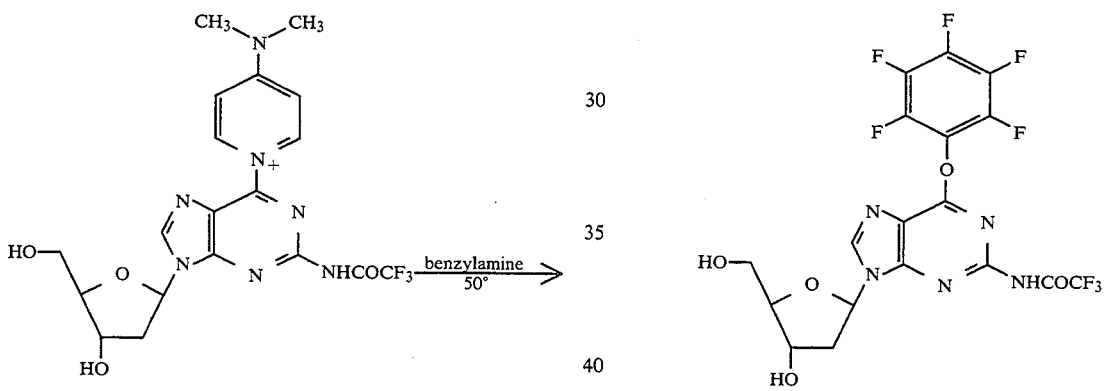

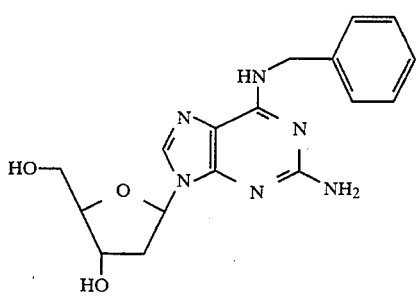

EXAMPLE XIV

Synthesis of O⁶-methyl-2'-deoxyguanosine.

To 2-amino-6-(4dimethylaminopyridyl)-9-(2-deoxy-beta-D-erythro-pentofuranoxsyl)purine or 2-N-trifluoroacetamido-6-pentafluorophenoxy-9-(2-deoxy-beta-D-erythro-pentofuranoxsyl)purine dissolved or suspended in methanol was added excess base, either triethylamine for the former or DBU (1,8-diazabicyclo[5.4.0]undec-7-ene] for the latter. After stirring at room temperature for several days or heating to 50° complete conversion to the product was effected.

The principles, preferred embodiments, and modes of operation of the present invention have been described in the foregoing specification. The invention which is intended to be protected herein, however, is not to be construed as limited to the particular embodiments disclosed, since these are to be regarded as illustrative rather than restrictive. Variations and changes may be made by others without departing from the spirit and scope of the invention.

What is claimed is:

1. The compound 2-N-trifluoroacetamido-6-(4-nitrophenoxy)-9-(2-deoxy-beta-D-erythro-pentofuranosyl)-purine.

2. The compound 2-N-trifluoroacetamido-6-(4-nitrophenoxy)-9-(beta-D-ribofuranosyl)purine.

3. The compound 2-N-trifluoracetamido-6-(meta-nitrophenoxy)-9-(2-deoxy-beta-D erythro-pentofuranosyl)purine.

4. The compound 2-N-trifluoroacetamido-6-(meta-nitrophenoxy)-9-(beta-D-ribofuranosyl)purine.

5. The compound 2-N-trifluoroacetamido-6-pentafluorophenoxy-9-(2-deoxy-beta-D-erythro-pentofuranosyl)purine.

6. The compound 2-N-trifluoroacetamido-6-pentafluorophenoxy-9-(beta-D-ribofuranosyl)purine.

7. The compound 6-dialkylaminopyridinium-9-(2-deoxy-beta-D-erythro-pentofuranosyl)purine.

8. The compound 6-dimethylaminopyridinium-9-(2-deoxy-beta-D-erythro-pentofuranosyl)purine.

9. The compound 6-dialkylaminopyridinium-9-(beta-D-ribofuranosyl)purine.

10. The compound 6-dimethylaminopyridinium-9-(beta-D-ribopentofuranosyl)purine.

11. A compound of formula I

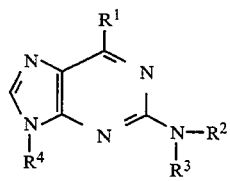
(I)

wherein $R^1$ is a nucleophile capable of binding to position 6 of the purine ring system without cleaving $R^2$ and is selected from the group consisting of 1) a nitrophenoxy group having a structure of

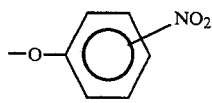

wherein said nitro group is in the 3,4 or 5 position;

2) a halophenoxy having the structure of formula II

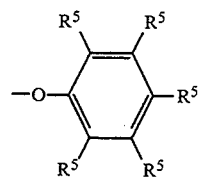
(II)

wherein $R^5$ is a halogen or hydrogen and at least three of said $R^5$ groups are halogens;

3) an aromatic tertiary amine; and 4) an aliphatic tertiary amine;

$R^2$ is selected from the group consisting of hydrogen; an aliphatic group having from 1 to 20 carbon atoms; an aromatic group having from 1 to 20 carbon atoms; and an amine protecting group, wherein said protecting group is an electron-withdrawing acyl group whose corresponding carboxylic acid as a $pK_a$ of less than that of acetic acid;

$R^3$ is selected from the group consisting of hydrogen; an aliphatic group having from 1 to 20 carbon atoms; an aromatic group having from 1 to 20 carbon atoms; and an amine protecting group, wherein said protecting group is an electron-withdrawing acyl group whose corresponding carboxylic acid has a $pK_a$ of less than that of acetic acid; and $R^4$ is selected from the group consisting of hydrogen, ribose, deoxyribose, substituted ribose and substituted deoxyribose, wherein the said substituent is selected from the group consisting of monophosphate, diphosphate, triphosphate, hydroxyl, and a hydroxyl protecting group.

12. The compound of claim 11, wherein $R^2$ is an aliphatic or aromatic acyl group.

13. The compound of claim 12, wherein $R^2$ is monohaloacetyl, dihaloacetyl, or trihaloacetyl.

14. The compound of claim 13, wherein $R^2$ is trifluoroacetyl.

15. The compound of claim 11, wherein said hydroxyl protecting group comprises $R^6X_2CCOO-$, wherein each X is hydrogen or a halogen, and $R^6$ is selected from the group consisting of an aliphatic group of between 1 and about 20 carbon atoms, trityl, $(CH_3)_3C(CH_3)_2SiO-$, toluyl, benzyl, isobutyryl, tert-butyldiarylsilyl, tert-butyldialkylsilyl, $COCH_2CH_2COMe$, bis (diisopropylamino) methoxyphosphine, and compounds having a structure in the formula of (III-V):

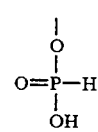
III

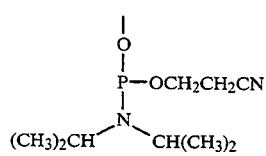
IV

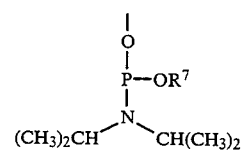
V wherein $R^7$ is a phosphate protecting group.

16. The compound of claim 11, wherein said $R^4$ is deoxyribose.

17. The compound of claim 16, wherein said deoxyribose is substituted in a 3'- or 5'- position by a moiety selected from the group consisting of monophosphate, diphosphate, triphosphate, hydroxyl, and a hydroxy protecting group.

18. The compound of claim 11, wherein said $R^4$ is ribose.

19. The compound of claim 18, wherein said ribose is substituted in a 3'-, 5'- or 2'- position by a moiety selected from the group consisting of monophosphate, diphosphate, triphosphate, hydroxyl, and a hydroxyl protecting group.

20. The compound of claim 11, wherein $R^1$ is selected from the group consisting of 1) a 4-dimethylaminopyridinium having the formula

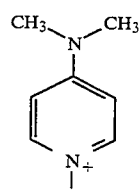

2) a nitrophenoxy having said nitro group in the 3, 4, or 5 position; and

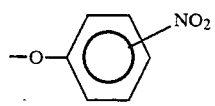

3) a pentafluorophenoxy.

21. The compound of claim 20, wherein said hydroxyl protecting group comprises $R^6X_2CCOO—$, wherein each X is hydrogen or a halogen, and $R^6$ is selected from the group consisting of an aliphatic group of between 1 and about 20 carbon atoms, trityl, $(CH_3)_3C(CH_3)_2SiO—$, toluyl, benzyl, isobutyryl, tert-butyldiarylsilyl, tert-butyldialkylsilyl, $COCH_2CH_2COMe$, bis(diisopropylamino) methoxyphosphine, and compounds having a structure in the formula of (III–V):

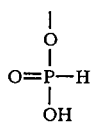  III

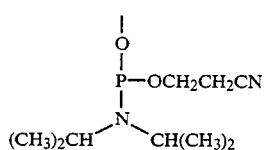  IV

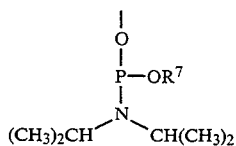  V wherein $R_7$ is a phosphate protecting group.

22. The compound of claim 21, wherein said $R^4$ is deoxyribose.

23. The compound of claim 22, wherein said deoxyribose is substituted in a 3'- or 5'-position by a moiety selected from the group consisting of monophosphate, diphosphate, triphosphate, hydroxyl, and a hydroxyl protecting group.

24. The compound of claim 21, wherein said $R^4$ is ribose.

25. The compound of claim 24, wherein said ribose is substituted in a 3'-, 5'- or 2'-position by a moiety selected from the group consisting of monophosphate, diphosphate, triphosphate, hydroxyl, and a hydroxyl protecting group.

26. The compound of claim 11, wherein said $R^4$ is hydrogen.

27. An oligonucleotide having a structure of the formula (VI):

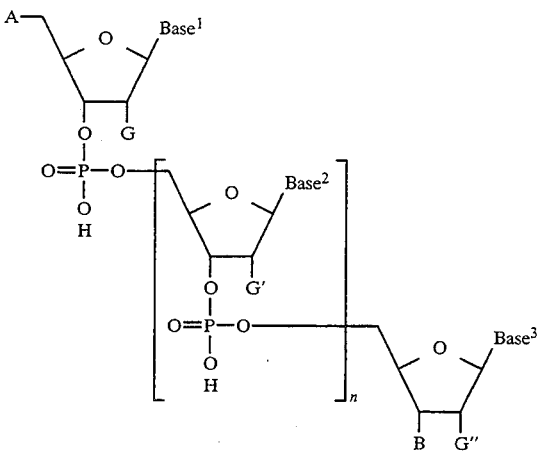

wherein n is 0 or a positive integer and wherein G, G' and G" may be the same or different and are hydrogen, hydroxyl, or a protected hydroxyl group;

Base1, Base2 and Base3 may be the same or different and are purine or pyrimidine bases, wherein at least one of said Bases has a structure of the formula (VII):

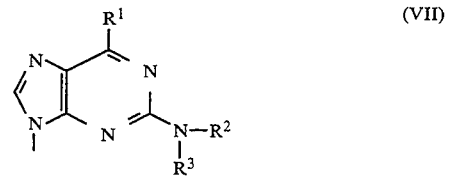  (VII)

wherein $R^1$ is a nucleophile capable of binding to position 6 of the purine ring system without cleaving $R^2$ and is selected from the group consisting of
1) a nitrophenoxy having the structure

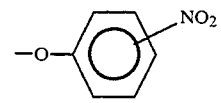

wherein said nitro group is in the 3, 4 or 5 position;
2) a halophenoxy having the structure of

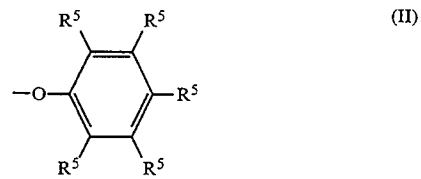  (II)

wherein $R^5$ is a halogen or hydrogen and at least three of the $R^5$ groups are halogens;
3) an aromatic tertiary amine; and
4) an aliphatic tertiary amine;
$R^2$ is selected from the group consisting of hydrogen an aliphatic group having from carbon atoms, an aromatic group having form 1 to 20 carbon atoms, and an amine protecting group, wherein said protecting group is an electron-withdrawing acyl group whose corresponding carboxylic acid has a $pK_a$ of less than that of acetic acid;

$R^3$ is selected from the group consisting of hydrogen; aliphatic group having form 1 to 20 carbon atoms; an aromatic group having form 1 to 20 carbon atoms; and an amine protecting group wherein said protecting group is an electron-withdrawing acyl group whose corresponding carboxylic acid has a $pK_a$ less than that of acetic acid;

A is a hydroxyl protecting group; hydroxyl, hydrogen, monophosphate, diphosphate or triphosphate; and B is a hydroxyl protecting group, hydroxyl, hydrogen, monophosphate, diphosphate or triphosphate.

28. The compound of claim 27, wherein said $R^2$ is an aliphatic or aromatic acyl group.

29. The compound of claim 28, wherein said $R^2$ is monohaloacetyl, dihaloacetyl, or trihaloacetyl.

30. The compound of claim 29, wherein $R^2$ is trifluoracetyl.

31. The compound of claim 27, wherein said protecting group A or said protecting group B will inhibit a reaction of the saccharide in the position being protected and which may be removed by hydrolysis.

32. The compound of claim 31, wherein said protecting group comprises $R^6X_2CCOO$— wherein each X is hydrogen or a halogen, and $R^6$ is selected from the group consisting of an aliphatic group of between 1 and about 20 carbon atoms, trityl, $(CH_3)_3C(CH_3)_2SiO$—, toluyl, benzyl, isobutyryl, tert-butyldiarylsilyl, tert-butyldialkylsilyl, $COCH_2CH_2COMe$, bis(diisopropylamino) methoxyphosphine, and compounds having a structure in the formula of (III-V):

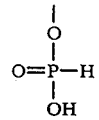

III

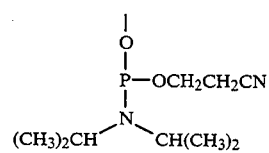

IV

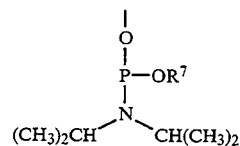

V wherein $R^7$ is a phosphate protecting group.

* * * * *

UNITED STATES PATENT AND TRADEMARK OFFICE
CERTIFICATE OF CORRECTION

PATENT NO. : 5,412,088

DATED : May 2, 1995

INVENTOR(S) : Jones et al.

Page 1 of 4

It is certified that error appears in the above-indentified patent and that said Letters Patent is hereby corrected as shown below:

On cover page after [75] Inventors: "Fathip" should read --Fathi--.

Column 2, line 66, "Synthysis" should read --Synthesis--.

Column 2, line 67, "2-Deoxyguansine" should read --2-Deoxyguanosine--.

Column 3, line 6, "3',5' -di-O-methyoxyacetyl-2'deoxyguanosine" should read --3'5'-di-O-methoxyacetyl-2'-deoxyguanosine--.

Column 3, line 45, "succeptability" should read --susceptibility--.

Column 4, line 27, "$N^2$ amino" should read --$N^{2-}$amino--.

Column 6, line 11, "pentofuransoyl)pyrine" should read --pentofuranosyl)purine--.

Column 6, line 17, "trifluoracetamide" should read --trifluoroacetamido--.

Column 7, line 43, "quanosine" should read --guanosine--.

Column 8, line 2, "carboxcylic" should read --carboxylic--.

Column 8, line 44, "have an" should read --have a--.

UNITED STATES PATENT AND TRADEMARK OFFICE
CERTIFICATE OF CORRECTION

PATENT NO.  : 5,412,088
DATED       : May 2, 1995
INVENTOR(S) : Jones et al.

Page 2 of 4

It is certified that error appears in the above-indentified patent and that said Letters Patent is hereby corrected as shown below:

Column 14, line 32, "2thiouracil" should read --2-thiouracil,--.

Column 16, line 13, "promoted" should read --promote--.

Column 17, line 26, "[$H_3O+$].fH." should read --[$H_3O+$]·fH.--.

Column 21, line 9, "d[TT(2-NH2-A)TT]" should read --d[TT(2-$NH_2$-A)TT]--.

Column 21, line 12, "B-CYANOETHYL     PHOSPHORAMIDITE" should read --B-CYANOETHYL PHOSPHORAMIDITE--.

Column 29, line 61, "281" should read --248--.

Column 29, line 66, "(m, 2, $H_{5'},5'$)," should read (m, 2, $H_{5'},5"$),--

Column 29, line 66, "$C_{11}H_{15}N_5O_4$·$H_2O$:" should read --$C_{11}H_{15}N_5O_4$·$H_2O$:--.

Column 30, line 22, "283 nm;" should read --283 $_{nm}$;--

Column 30, lines 25 and 26, "2.55" should appear on one line.

UNITED STATES PATENT AND TRADEMARK OFFICE
CERTIFICATE OF CORRECTION

PATENT NO. : 5,412,088

DATED : May 2, 1995

INVENTOR(S) : Jones et al.

It is certified that error appears in the above-indentified patent and that said Letters Patent is hereby corrected as shown below:

Column 30, lines 32 and 33, "bid-O-(tert-butyldimethslsiyl)" should read --bis-O-tert-butyldimethylsilyl)--.

Column 30, lines 35 and 36, "dimethylsilyldeoxyguono-sine," should read --dimethylsilyl-deoxyguanosine,--.

Column 30, line 47, bid-O-tert-butyldimethyslsilyl)" should read --bis-O-(tert-butyldimethylsilyl)--.

Column 31, line 14, "$C_{10}H_{14}N_6O_3.H_2O$:" should read --$C_{10}H_{14}N_6O_3 \cdot H_2O$--.

Column 33, line 51, "$PCL_3$" should read --$PCl_3$--.

Column 33, line 53, "$PCL_3$" should read --$PCl_3$".

Column 34, line 12, insert "." after "derivative".

Column 38, line 38, "trifluoracetamido" should read --trifluoroacetamido--.

Column 40, line 58, "trifluoracetamido" should read --trifluoroacetamido--.

Column 41, line 50 "as" should rad --has--.

Column 42, line 43, "hydroxy" should read --hydroxyl--.

UNITED STATES PATENT AND TRADEMARK OFFICE
CERTIFICATE OF CORRECTION

PATENT NO. : 5,412,088
DATED : May 2, 1995
INVENTOR(S) : Jones et al.

It is certified that error appears in the above-indentified patent and that said Letters Patent is hereby corrected as shown below:

Column 44, line 64, "form" should read --from--.

Column 45, line 2, "form" should read --from--.

Column 45, line 3, "form" should read --from--.

Column 45, lines 17, 18, "tri-fluoracetyl" should read --trifluoroacetyl--.

Signed and Sealed this

Fourteenth Day of November, 1995

Attest:

BRUCE LEHMAN

Attesting Officer

Commissioner of Patents and Trademarks